(12) United States Patent
Geller et al.

(10) Patent No.: US 7,790,694 B2
(45) Date of Patent: Sep. 7, 2010

(54) ANTISENSE ANTIBACTERIAL METHOD AND COMPOUND

(75) Inventors: Bruce L. Geller, Corvallis, OR (US); Patrick L. Iversen, Corvallis, OR (US); Lucas D. Tilley, Burlington, VT (US)

(73) Assignee: AVI BioPharma Inc., Corvallis, OR (US)

( * ) Notice: Subject to any disclaimer, the term of this patent is extended or adjusted under 35 U.S.C. 154(b) by 325 days.

(21) Appl. No.: 11/487,009

(22) Filed: Jul. 13, 2006

(65) Prior Publication Data
US 2007/0135333 A1 Jun. 14, 2007

Related U.S. Application Data

(60) Provisional application No. 60/699,280, filed on Jul. 13, 2005.

(51) Int. Cl.
C07H 21/02 (2006.01)
C07H 21/04 (2006.01)
A61K 31/70 (2006.01)
C12N 5/00 (2006.01)
C12Q 1/68 (2006.01)

(52) U.S. Cl. .................. 514/44 A; 435/6; 536/23.1; 536/24.1; 536/24.5

(58) Field of Classification Search .............. None
See application file for complete search history.

(56) References Cited

U.S. PATENT DOCUMENTS

| | | | |
|---|---|---|---|
| 5,034,506 A | 7/1991 | Summerton et al. | |
| 5,142,047 A | 8/1992 | Summerton et al. | |
| 5,166,315 A | 11/1992 | Summerton et al. | |
| 5,185,444 A | 2/1993 | Summerton et al. | |
| 5,217,866 A | 6/1993 | Summerton et al. | |
| 5,506,337 A | 4/1996 | Summerton et al. | |
| 5,521,063 A | 5/1996 | Summerton et al. | |
| 5,580,767 A | 12/1996 | Cowsert et al. | |
| 5,698,685 A | 12/1997 | Summerton et al. | |
| 6,060,456 A | 5/2000 | Arnold et al. | |
| 6,133,246 A | 10/2000 | McKay et al. | |
| 6,228,579 B1 | 5/2001 | Zyskind et al. | |
| 6,239,265 B1 | 5/2001 | Cook | |
| 6,365,351 B1 | 4/2002 | Iversen | |
| 6,495,663 B1 | 12/2002 | Rothbard | |
| 6,548,651 B1 | 4/2003 | Nielsen et al. | |
| 6,677,153 B2 | 1/2004 | Iversen | |
| 6,828,105 B2 | 12/2004 | Stein et al. | |
| 6,841,542 B2 | 1/2005 | Bartelmez et al. | |
| 7,049,431 B2 | 5/2006 | Iversen et al. | |
| 7,094,765 B1 | 8/2006 | Iversen et al. | |
| 7,625,873 B2 | 12/2009 | Geller et al. | 514/44 |
| 2004/0110296 A1 | 6/2004 | Vargeese et al. | |
| 2006/0148747 A1 | 7/2006 | Stein et al. | |
| 2007/0021362 A1 | 1/2007 | Geller et al. | 514/44 |
| 2008/0194463 A1 | 8/2008 | Weller et al. | 514/44 |

FOREIGN PATENT DOCUMENTS

| | | |
|---|---|---|
| WO | WO 01/49775 A2 | 7/2001 |
| WO | WO 02/079467 A2 | 10/2002 |

OTHER PUBLICATIONS

Anderson et al., *Antimicrobial Agents and Chemotherapy*, 40(9):2004-2011 (1996).
Blommers et al., *Nucleic Acids Res*, 22(20):4187-4194 (1994).
Bramhill et al. *Annu Rev Cell Dev Biol.*, 13:395-424 (1997).
Cross, C. W., J. S. Rice, et al. (1997). "Solution structure of an RNA×DNA hybrid duplex containing a 3'-thioformacetal linker and an RNA A-tract." *Biochemistry* 36(14): 4096-107.
Donachie, W.D. (1993). *Annu. Rev. Microbiol.*, 47:199-230.
Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* 0(14): 1684-6.
Geller et al., *Antimicrobial Agents and Chemotherapy*, 47(10):3233-3239 (2003).
Geller et al., *J. Biol. Chem.*, 264(28):16465-16469 (1989).
Geller et al., *J. of Antimicrobial Chemotherapy.*, 55:983-988 (2005).
Gerdes et al., *J. Bacteriol.*, 185(19):5673-5684 (2003).
Good et al., *Nature Biotechnology*, 19(4):360-364 (2001).
Good et al., *PNAS*, 95:2073-2076 (1998).
Hale et al., *J. Bacteriol.*, 181(1):167-176 (1999).
Lesnikowski, Z. J., M. Jaworska, et al., "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15 (1990).
Lutkenhaus, J. and Addinall, S.G., *Annu. Rev. Biochem.*, 66:93-116 (1997).
Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem* 12(1): 154-7.
Pari et al., *Antimicrobial Agents and Chemotherapy*, 39(5):1157-1161 (1995).

(Continued)

*Primary Examiner*—Sean R McGarry
(74) *Attorney, Agent, or Firm*—Seed IP Law Group PLLC

(57) ABSTRACT

An antibacterial antisense conjugate and method of using the same for treating a bacterial infection in a mammalian host are disclosed. The conjugate includes an antisense oligonucleotide conjugated to a carrier peptide that significantly enhances the antibacterial activity of the oligonucleotide. The antisense oligonucleotide contains 10-20 nucleotide bases and has a targeting nucleic acid sequence complementary to a target sequence containing or within 10 bases, in a downstream direction, of the translational start codon of a bacterial mRNA that encodes a bacterial protein essential for bacterial replication, where the compound binds to a target mRNA with a $T_m$ of between 50° to 60° C. The carrier peptide is an arginine-rich peptide containing between 6 and 12 amino acids.

8 Claims, 18 Drawing Sheets

OTHER PUBLICATIONS

Rahman et al., *Antisense Research and Development*, 1:319-327 (1991).

Summerton, J. and D. Weller (1997). "Morpholino antisense oligomers: design, preparation, and properties." Antisense Nucleic Acid Drug Dev 7(3): 187-95.

Summerton et al., *Antisense & Nucleic Acid Drug Development*, 7:63-70 (1997).

Tan et al., *Antimicrobial Agents and Chemotherapy*, 49(8):3202-3207 (2005).

Tilley et al., *Antimicrobial Agents and Chemotherapy*, 50(8):2789-2796 (2006).

Zhang, Y and Cronan, J.E., *J. Bacteriology*, 178(12):3614-3620 (1996).

PCT/US2005/023553, AVI Biopharma, Inc., Nov. 8, 2006.

Deere et al., *Antimicrobial Agents and Chemotherapy*, 49(1):249-255 (2005).

Dryselius et al., *Oligonucleotides*, 13(6):427-33 (2003).

Nielsen, P. E., *Expert Opinion on Investigational Drugs*, 10(2):331-341 (2001).

Wang et al., *FEMS Microbiology Letters*, 220(2):171-176 (2003).

Mellbye, B.L. et al., "Variations in amino acid composition of antisense peptide-phosphorodiamidate morpholino oligomer affect potency against *Escherichia coli* in vitro and in vivo", *Antimicrobial Agents and Chemotherapy*, 53(2):525-530 (2009).

Summerton, J.E., "Morpholinos and PNAs Compared", in "Peptide Nucleic Acids, Morpholinos, and Related Antisense Biomolecules", C.G. Janson and M.J. During, eds., Eurekah.com and Kluwer Academic/Plenum Publishers, 2006; pp. 89-113.

Moulton et al., "Cellular uptake of antisense morpholino oligomers conjugated to arginine-rich peptides," Bioconjugate Chem. 15:290:299, 2004.

Moulton et al., "HIV Tat peptide enhances cellular delivery of antisense morpholino oligomers," Antisense Nucleic Acid Drug Dev. 13:31-43, 2003.

Moulton et al., "Peptide-assisted delivery of steric-blocking antisense oligomers," Curr. Opin. Mol. Ther. 5(2):123-132, 2003.

Nelson et al, "Arginine-rich peptide conjugation to morpholino oligomers: effects on antisense activity and specificity," Bioconjugate Chem. 16:959-966, 2005.

Rothbard et al. "Arginine-Rich Molecular Transporters for Drug Delivery: Role of Backbone Spacing in Cellular Uptake," J. Med. Chem. 45:3612-3618, 2002.

Geller, et al., "Antisense Antibacterial Method and Compound," U.S. Appl. No. 12/723,035, filed Mar. 12, 2010.

Geller, et al., "Antisense Antibacterial Oligonucleotide and Method," U.S. Appl. No. 12/723,413, filed Mar. 12, 2010.

Geller, et al., "Antisense Antibacterial Method and Compound," U.S. Appl. No. 12/613,428, filed Nov. 5, 2009.

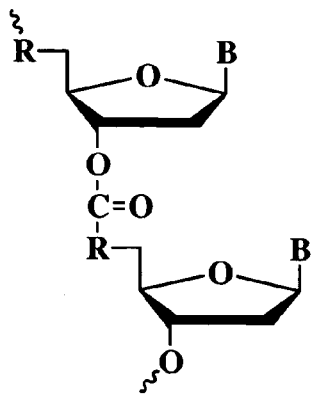
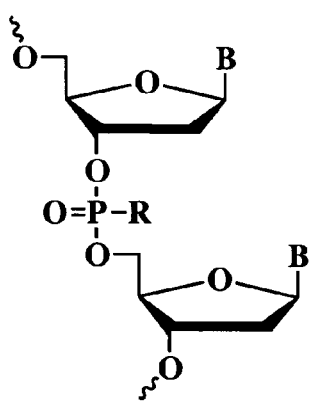
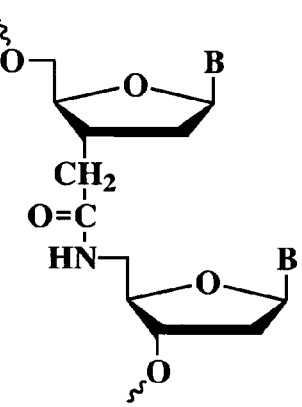
Fig. 2A  Fig. 2B  Fig. 2C
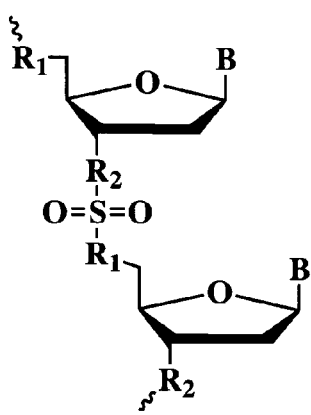
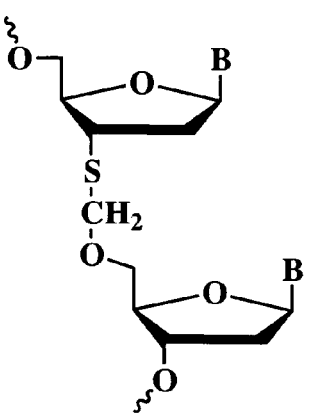
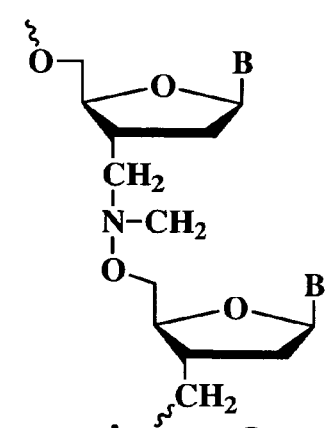
Fig. 2D  Fig. 2E  Fig. 2F
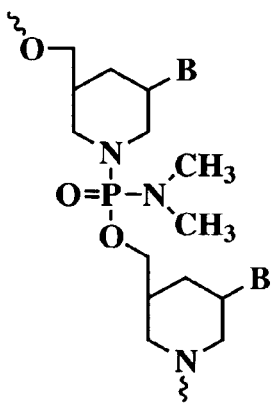
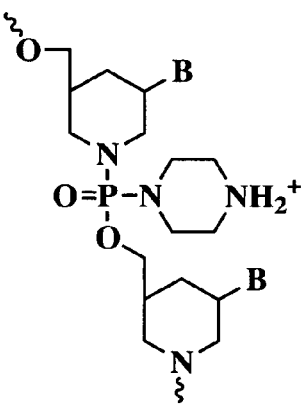
Fig. 2G  Fig. 2H

SEQUENCE LISTING

```
<160> NUMBER OF SEQ ID NOS: 96

<210> SEQ ID NO 1
<211> LENGTH: 31
<212> TYPE: DNA
<213> ORGANISM: Escherichia coli

<400> SEQUENCE: 1
gagagaaact atgtttgaac caatggaact t                               31

<210> SEQ ID NO 2
<211> LENGTH: 31
<212> TYPE: DNA
<213> ORGANISM: Escherichia coli

<400> SEQUENCE: 2
atttaagagt atgagcacta tcgaagaacg c                               31

<210> SEQ ID NO 3
<211> LENGTH: 31
<212> TYPE: DNA
<213> ORGANISM: Escherichia coli

<400> SEQUENCE: 3
tagcggttag atgagcgacc ttgcgagagaa                                31

<210> SEQ ID NO 4
<211> LENGTH: 31
<212> TYPE: DNA
<213> ORGANISM: Escherichia coli

<400> SEQUENCE: 4
```

```
gagagaaact atgtttgaac caatggaact t                              31

<210> SEQ ID NO 5
<211> LENGTH: 31
<212> TYPE: DNA
<213> ORGANISM: Escherichia coli

<400> SEQUENCE: 5
atttaagagt atgagcacta tcgaagaacg c                              31

<210> SEQ ID NO 6
<211> LENGTH: 31
<212> TYPE: DNA
<213> ORGANISM: Escherichia coli

<400> SEQUENCE: 6
tagcggttag atgagcgacc ttgcgagagaa                               31

<210> SEQ ID NO 7
<211> LENGTH: 31
<212> TYPE: DNA
<213> ORGANISM: Salmonella typhimurium

<400> SEQUENCE: 7
gagagagatt atgtttgaac ctatggaact a                              31

<210> SEQ ID NO 8
<211> LENGTH: 31
<212> TYPE: DNA
<213> ORGANISM: Salmonella typhimurium

<400> SEQUENCE: 8
atttaagagt atgagcacta tcgaagaacg c                              31

<210> SEQ ID NO 9
<211> LENGTH: 31
<212> TYPE: DNA
<213> ORGANISM: Salmonella typhimurium

<400> SEQUENCE: 9
tagcggttag atgagcgacc ttgcgagagaa                               31

<210> SEQ ID NO 10
<211> LENGTH: 30
<212> TYPE: DNA
<213> ORGANISM: Pseudomonas aeruginosa

<400> SEQUENCE: 10 gagagggaa atgtttgaac tggtcgataa                                 30

<210> SEQ ID NO 11
<211> LENGTH: 31
<212> TYPE: DNA
<213> ORGANISM: Pseudomonas aeruginosa

<400> SEQUENCE: 11
aaaacaaggt atgagcacca tcgaagaacgc                               31

<210> SEQ ID NO 12
<211> LENGTH: 31
<212> TYPE: DNA
<213> ORGANISM: Pseudomonas aeruginosa
```

-continued

```
<400> SEQUENCE: 12
caggcttctc atgggcgaac tggccaaagaa                              31

<210> SEQ ID NO 13
<211> LENGTH: 31
<212> TYPE: DNA
<213> ORGANISM: Vibrio cholera

<400> SEQUENCE: 13
gagataacac atgtttgaac cgatgatgga a                             31

<210> SEQ ID NO 14
<211> LENGTH: 31
<212> TYPE: DNA
<213> ORGANISM: Vibrio cholera

<400> SEQUENCE: 14
actatattgg atggtttata tgtctatctc t                             31

<210> SEQ ID NO 15
<211> LENGTH: 31
<212> TYPE: DNA
<213> ORGANISM: Vibrio cholera

<400> SEQUENCE: 15
taatggctct atgagcgatc tagctaaaga g                             31

<210> SEQ ID NO 16
<211> LENGTH: 30
<212> TYPE: DNA
<213> ORGANISM: Neisseria gonorrhoea

<400> SEQUENCE: 16 gagttttga atggaatttg tttacgacgt                                30

<210> SEQ ID NO 17
<211> LENGTH: 30
<212> TYPE: DNA
<213> ORGANISM: Neisseria gonorrhoea

<400> SEQUENCE: 17
aacgactgat atgtcaaaca tcgaacaaca                               30

<210> SEQ ID NO 18
<211> LENGTH: 30
<212> TYPE: DNA
<213> ORGANISM: Neisseria gonorrhoea

<400> SEQUENCE: 18
cattgaaacc atgaccgacg caaccatccg                               30

<210> SEQ ID NO 19
<211> LENGTH: 31
<212> TYPE: DNA
<213> ORGANISM: Staphylococcus aureus

<400> SEQUENCE: 19
ggaaatttaa atgttagaat ttgaacaagg a                             31

<210> SEQ ID NO 20
<211> LENGTH: 31
<212> TYPE: DNA
<213> ORGANISM: Staphylococcus aureus
```

<400> SEQUENCE: 20
ggaactcttg atggctgaat tacctcaatc a                                31

<210> SEQ ID NO 21
<211> LENGTH: 30
<212> TYPE: DNA
<213> ORGANISM: Staphylococcus aureus

<400> SEQUENCE: 21
atcataaatc atggaaaaga tgcatatcac                                  30

<210> SEQ ID NO 22
<211> LENGTH: 31
<212> TYPE: DNA
<213> ORGANISM: Mycobacterium tuberculosis

<400> SEQUENCE: 22
ctctaagcct atggttgagg ttgagagttt g                                31

<210> SEQ ID NO 23
<211> LENGTH: 31
<212> TYPE: DNA
<213> ORGANISM: Mycobacterium tuberculosis

<400> SEQUENCE: 23
cccgggcgcg atgtggcgat atccactaagt                                 31

<210> SEQ ID NO 24
<211> LENGTH: 31
<212> TYPE: DNA
<213> ORGANISM: Mycobacterium tuberculosis

<400> SEQUENCE: 24
cgaggaatag atgacagaca cgacgttgccg                                 31

<210> SEQ ID NO 25
<211> LENGTH: 30
<212> TYPE: DNA
<213> ORGANISM: Mycobacterium tuberculosis

<400> SEQUENCE: 25
ggaaagcctg atgcggatcg gcatgatttg                                  30

<210> SEQ ID NO 26
<211> LENGTH: 30
<212> TYPE: DNA
<213> ORGANISM: Mycobacterium tuberculosis

<400> SEQUENCE: 26
ctggcacgtc gtgaccgatc gggctcgctt                                  30

<210> SEQ ID NO 27
<211> LENGTH: 31
<212> TYPE: DNA
<213> ORGANISM: Helicobacter pylori

<400> SEQUENCE: 27
gaatgtggct atggttcatc aatcagagat g                                31

<210> SEQ ID NO 28
<211> LENGTH: 31
<212> TYPE: DNA

-continued

<213> ORGANISM: Helicobacter pylori

<400> SEQUENCE: 28
agttttaatt atggctttat ttgaagatat t          31

<210> SEQ ID NO 29
<211> LENGTH: 31
<212> TYPE: DNA
<213> ORGANISM: Helicobacter pylori

<400> SEQUENCE: 29
agggagacac atgcaagata attcagtcaa t          31

<210> SEQ ID NO 30
<211> LENGTH: 31
<212> TYPE: DNA
<213> ORGANISM: Streptococcus pneumoniae

<400> SEQUENCE: 30
aaaataaatt atgacatttt catttgatac a          31

<210> SEQ ID NO 31
<211> LENGTH: 31
<212> TYPE: DNA
<213> ORGANISM: Streptococcus pneumoniae

<400> SEQUENCE: 31
gagtcctatc atggcagtat ttgaaaaagt a          31

<210> SEQ ID NO 32
<211> LENGTH: 31
<212> TYPE: DNA
<213> ORGANISM: Streptococcus pneumoniae

<400> SEQUENCE: 32
gcatttatta atgcaggata aaaatttagt g          31

<210> SEQ ID NO 33
<211> LENGTH: 31
<212> TYPE: DNA
<213> ORGANISM: Treponema palladium

<400> SEQUENCE: 33
tgggagggga atgatgaata tagagcttgca          31

<210> SEQ ID NO 34
<211> LENGTH: 31
<212> TYPE: DNA
<213> ORGANISM: Treponema palladium

<400> SEQUENCE: 34
tgccccgtgg atgagttgtt cttaagaatg a          31

<210> SEQ ID NO 35
<211> LENGTH: 31
<212> TYPE: DNA
<213> ORGANISM: Treponema palladium

<400> SEQUENCE: 35
tgcccgccct atggaagaaa ttagcacccca          31

<210> SEQ ID NO 36
<211> LENGTH: 31

```
<212> TYPE: DNA
<213> ORGANISM: Chlamydia trachomatis

<400> SEQUENCE: 36
ggatcatagg atgagtttag aagatgatgt a                              31

<210> SEQ ID NO 37
<211> LENGTH: 31
<212> TYPE: DNA
<213> ORGANISM: Chlamydia trachomatis

<400> SEQUENCE: 37
aaacgaactt atgagcgacc tctcggacct a                              31

<210> SEQ ID NO 38
<211> LENGTH: 29
<212> TYPE: DNA
<213> ORGANISM: Bartonella henselae

<400> SEQUENCE: 38
aggcaaatta attggtaaaa aattagaga                                 29

<210> SEQ ID NO 39
<211> LENGTH: 30
<212> TYPE: DNA
<213> ORGANISM: Bartonella henselae

<400> SEQUENCE: 39
ggatttcaac atgagtgata cagtagagcg                                30

<210> SEQ ID NO 40
<211> LENGTH: 30
<212> TYPE: DNA
<213> ORGANISM: Bartonella henselae

<400> SEQUENCE: 40
gtctaaagct gtgacagatc taaacccgca                                30

<210> SEQ ID NO 41
<211> LENGTH: 31
<212> TYPE: DNA
<213> ORGANISM: Haemophilus influenzae

<400> SEQUENCE: 41
gagaacatca atgctatacc cagagtaccc t                              31

<210> SEQ ID NO 42
<211> LENGTH: 31
<212> TYPE: DNA
<213> ORGANISM: Haemophilus influenzae

<400> SEQUENCE: 42
ggaaaaacaa atgagtattg aagaacgcgtg                               31

<210> SEQ ID NO 43
<211> LENGTH: 31
<212> TYPE: DNA
<213> ORGANISM: Haemophilus influenzae

<400> SEQUENCE: 43
aggaatacca atgacggatt caatccaatc a                              31

<210> SEQ ID NO 44
```

```
<211> LENGTH: 30
<212> TYPE: DNA
<213> ORGANISM: Listeria monocytogenes

<400> SEQUENCE: 44
aggcaataat atgttagaat ttgacactag                                    30

<210> SEQ ID NO 45
<211> LENGTH: 30
<212> TYPE: DNA
<213> ORGANISM: Listeria monocytogenes

<400> SEQUENCE: 45
cgaacgcata aaactttatg tgaccggata                                    30

<210> SEQ ID NO 46
<211> LENGTH: 30
<212> TYPE: DNA
<213> ORGANISM: Listeria monocytogenes

<400> SEQUENCE: 46
ttctctaaca atggcagaaa caccaaatca                                    30

<210> SEQ ID NO 47
<211> LENGTH: 30
<212> TYPE: DNA
<213> ORGANISM: Yersinia pestis

<400> SEQUENCE: 47
gagagaaact atgtttgaac ctatggaact                                    30

<210> SEQ ID NO 48
<211> LENGTH: 30
<212> TYPE: DNA
<213> ORGANISM: Yersinia pestis

<400> SEQUENCE: 48
atttaagagt atgagcacta tcgaagaacg                                    30

<210> SEQ ID NO 49
<211> LENGTH: 30
<212> TYPE: DNA
<213> ORGANISM: Yersinia pestis

<400> SEQUENCE: 49
tagcggctca atgagcgacc ttgccagaga                                    30

<210> SEQ ID NO 50
<211> LENGTH: 30
<212> TYPE: DNA
<213> ORGANISM: Bacillus anthracis

<400> SEQUENCE: 50
ggatttcgac atgttagagt ttgatactac                                    30

<210> SEQ ID NO 51
<211> LENGTH: 30
<212> TYPE: DNA
<213> ORGANISM: Bacillus anthracis

<400> SEQUENCE: 51
ggtgaatgga atggcagatg ttttagagcg                                    30
```

-continued

```
<210> SEQ ID NO 52
<211> LENGTH: 30
<212> TYPE: DNA
<213> ORGANISM: Bacillus anthracis

<400> SEQUENCE: 52
gtgctcgttg atgtcagaca atcaacaaca                                    30

<210> SEQ ID NO 53
<211> LENGTH: 30
<212> TYPE: DNA
<213> ORGANISM: Burkholderia mallei

<400> SEQUENCE: 53
ggaggcaaca atggaattcg aaatgctgga                                    30

<210> SEQ ID NO 54
<211> LENGTH: 30
<212> TYPE: DNA
<213> ORGANISM: Burkholderia mallei

<400> SEQUENCE: 54
cggaggggta atggacaaca tcgaacaacg                                    30

<210> SEQ ID NO 55
<211> LENGTH: 30
<212> TYPE: DNA
<213> ORGANISM: Burkholderia mallei

<400> SEQUENCE: 55
atacggatac atggatcaat tcgccaaaga                                    30

<210> SEQ ID NO 56
<211> LENGTH: 30
<212> TYPE: DNA
<213> ORGANISM: Burkholderia pseudomallei

<400> SEQUENCE: 56
ggaggcaaca atggaattcg aaatgctgga                                    30

<210> SEQ ID NO 57
<211> LENGTH: 30
<212> TYPE: DNA
<213> ORGANISM: Burkholderia pseudomallei

<400> SEQUENCE: 57
cggaggggta atggacaaca tcgaacaacg                                    30

<210> SEQ ID NO 58
<211> LENGTH: 30
<212> TYPE: DNA
<213> ORGANISM: Burkholderia pseudomallei

<400> SEQUENCE: 58
atacggatac atggatcaat tcgccaaaga                                    30

<210> SEQ ID NO 59
<211> LENGTH: 30
<212> TYPE: DNA
<213> ORGANISM: Francisella tularensis

<400> SEQUENCE: 59
ggagtaaaat atgtttgatt ttaacgattc                                    30
```

```
<210> SEQ ID NO 60
<211> LENGTH: 30
<212> TYPE: DNA
<213> ORGANISM: Francisella tularensis

<400> SEQUENCE: 60
aggaaaaaat atgagtacac ataacgaaga                              30

<210> SEQ ID NO 61
<211> LENGTH: 30
<212> TYPE: DNA
<213> ORGANISM: Francisella tularensis

<400> SEQUENCE: 61
gcgataacta atgtctataa ttactaaaga                              30

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 62
ttcttcgata gtgctcatac                                         20

<210> SEQ ID NO 63
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 63
tcttcgatag tgctcata                                           18

<210> SEQ ID NO 64
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 64
cttcgatagt gctcat                                             16

<210> SEQ ID NO 65
<211> LENGTH: 14
<212> TYPE: DNA
<213> ORGANISM: Artificial Sequence
<220> FEATURE:
<223> OTHER INFORMATION: Synthetic Oligomer

<400> SEQUENCE: 65
tcgatagtgc tcat                                               14

<210> SEQ ID NO 66
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 66
cttcgatagt g                                                  11
```

-continued

<210> SEQ ID NO 67
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 67
ttcgatagtg                                                           10

<210> SEQ ID NO 68
<211> LENGTH: 9
<212> TYPE: DNA
<213> ORGANISM: Artificial Sequence
<220> FEATURE:
<223> OTHER INFORMATION: Synthetic Oligomer

<400> SEQUENCE: 68 ttcgatagt                                                             9

<210> SEQ ID NO 69
<211> LENGTH: 8
<212> TYPE: DNA
<213> ORGANISM: Artificial Sequence
<220> FEATURE:
<223> OTHER INFORMATION: Synthetic Oligomer

<400> SEQUENCE: 69 tcgatagt                                                              8

<210> SEQ ID NO 70
<211> LENGTH: 7
<212> TYPE: DNA
<213> ORGANISM: Artificial Sequence
<220> FEATURE:
<223> OTHER INFORMATION: Synthetic Oligomer

<400> SEQUENCE: 70 tcgatag                                                               7

<210> SEQ ID NO 71
<211> LENGTH: 6
<212> TYPE: DNA
<213> ORGANISM: Artificial Sequence
<220> FEATURE:
<223> OTHER INFORMATION: Synthetic Oligomer

<400> SEQUENCE: 71 cgatag                                                                6

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 72
ttgtcctgaa tatcacttcg                                                20

<210> SEQ ID NO 73
<211> LENGTH: 16
<212> TYPE: DNA
<213> ORGANISM: Artificial Sequence
<220> FEATURE:

-continued

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 73
gtcctgaata tcactt                                                     16

<210> SEQ ID NO 74
<211> LENGTH: 14
<212> TYPE: DNA
<213> ORGANISM: Artificial Sequence
<220> FEATURE:
<223> OTHER INFORMATION: Synthetic Oligomer

<400> SEQUENCE: 74
tcgtgagtat cact                                                       14

<210> SEQ ID NO 75
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 75
tctcagatgg t                                                          11

<210> SEQ ID NO 76
<211> LENGTH: 7
<212> TYPE: DNA
<213> ORGANISM: Artificial Sequence
<220> FEATURE:
<223> OTHER INFORMATION: Synthetic Oligomer

<400> SEQUENCE: 76 aatcgga                                                               7

<210> SEQ ID NO 77
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 77
acgttgaggc                                                            10

<210> SEQ ID NO 78
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 78
tccacttgcc                                                            10

<210> SEQ ID NO 79
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa = 6-aminohexanoic acid
<220> FEATURE:
<221> NAME/KEY: Xaa

```
<222> LOCATION: (11)..(11)
<223> OTHER INFORMATION: Xaa = beta-Alanine

<400> SEQUENCE: 79

Arg Phe Phe Arg Phe Phe Arg Phe Phe Xaa Xaa
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa = 6-aminohexanoic acid
<220> FEATURE:
<221> NAME/KEY: Xaa
<222> LOCATION: (12)..(12)
<223> OTHER INFORMATION: Xaa = beta-Alanine

<400> SEQUENCE: 80

Arg Thr Arg Thr Arg Phe Leu Arg Arg Thr Xaa Xaa
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa = 6-aminohexanoic acid
<220> FEATURE:
<221> NAME/KEY: Xaa
<222> LOCATION: (12)..(12)
<223> OTHER INFORMATION: Xaa = beta-Alanine

<400> SEQUENCE: 81

Arg Phe Phe Arg Phe Phe Arg Phe Phe Arg Xaa Xaa
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa = 6-aminohexanoic acid
<220> FEATURE:
<221> NAME/KEY: Xaa
<222> LOCATION: (12)..(12)
<223> OTHER INFORMATION: Xaa = beta-Alanine

<400> SEQUENCE: 82

Lys Thr Arg Thr Lys Phe Leu Lys Lys Thr Xaa Xaa
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: Xaa
<222> LOCATION: (10)..(10)
<223> OTHER INFORMATION: Xaa = 6-aminohexanoic acid
<220> FEATURE:
<221> NAME/KEY: Xaa
<222> LOCATION: (11)..(11)
<223> OTHER INFORMATION: Xaa = beta-Alanine

<400> SEQUENCE: 83

Lys Phe Phe Lys Phe Phe Lys Phe Phe Xaa Xaa
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa = 6-aminohexanoic acid
<220> FEATURE:
<221> NAME/KEY: Xaa
<222> LOCATION: (12)..(12)
<223> OTHER INFORMATION: Xaa = beta-Alanine

<400> SEQUENCE: 84

Lys Phe Phe Lys Phe Phe Lys Phe Phe Lys Xaa Xaa
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa = 6-aminohexanoic acid
<220> FEATURE:
<221> NAME/KEY: Xaa
<222> LOCATION: (8)..(8)
<223> OTHER INFORMATION: Xaa = beta-Alanine

<400> SEQUENCE: 85

Arg Phe Phe Arg Phe Phe Xaa Xaa
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa = 6-aminohexanoic acid
<220> FEATURE:
<221> NAME/KEY: Xaa
<222> LOCATION: (9)..(9)
<223> OTHER INFORMATION: Xaa = beta-Alanine

<400> SEQUENCE: 86

Arg Phe Phe Arg Phe Phe Arg Xaa Xaa
1               5

<210> SEQ ID NO 87
<211> LENGTH: 10
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (2)..(9)
<223> OTHER INFORMATION: Xaa = 6-aminohexanoic acid
<220> FEATURE:
<221> NAME/KEY: Xaa
<222> LOCATION: (10)..(10)
<223> OTHER INFORMATION: Xaa = beta-Alanine

<400> SEQUENCE: 87

Arg Xaa Xaa Arg Xaa Xaa Arg Xaa Xaa Xaa
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa = 6-aminohexanoic acid
<220> FEATURE:
<221> NAME/KEY: Xaa
<222> LOCATION: (11)..(11)
<223> OTHER INFORMATION: Xaa = beta-Alanine
<220> FEATURE:
<221> NAME/KEY: VARIANT
<222> LOCATION: (11)..(11)
<223> OTHER INFORMATION: amino acid conjugated to cttcgatagtg nucleotide
      sequence

<400> SEQUENCE: 88

Arg Phe Phe Arg Phe Phe Arg Phe Phe Xaa Xaa
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa = 6-aminohexanoic acid
<220> FEATURE:
<221> NAME/KEY: Xaa
<222> LOCATION: (12)..(12)
<223> OTHER INFORMATION: Xaa = beta-Alanine
<220> FEATURE:
<221> NAME/KEY: VARIANT
<222> LOCATION: (12)..(12)
<223> OTHER INFORMATION: amino acid conjugated to cttcgatagtg nucleotide
      sequence

<400> SEQUENCE: 89

Arg Thr Arg Thr Arg Phe Leu Arg Arg Thr Xaa Xaa
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
```

```
<222> LOCATION: (11)..(11)
<223> OTHER INFORMATION: Xaa = 6-aminohexanoic acid
<220> FEATURE:
<221> NAME/KEY: Xaa
<222> LOCATION: (12)..(12)
<223> OTHER INFORMATION: Xaa = beta-Alanine
<220> FEATURE:
<221> NAME/KEY: VARIANT
<222> LOCATION: (12)..(12)
<223> OTHER INFORMATION: amino acid conjugated to cttcgatagtg nucleotide
      sequence

<400> SEQUENCE: 90

Arg Phe Phe Arg Phe Phe Arg Phe Phe Arg Xaa Xaa
1               5                   10

<210> SEQ ID NO 91
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa = 6-aminohexanoic acid
<220> FEATURE:
<221> NAME/KEY: Xaa
<222> LOCATION: (8)..(8)
<223> OTHER INFORMATION: Xaa = beta-Alanine
<220> FEATURE:
<221> NAME/KEY: VARIANT
<222> LOCATION: (8)..(8)
<223> OTHER INFORMATION: amino acid conjugated to cttcgatagtg nucleotide
      sequence

<400> SEQUENCE: 91

Arg Phe Phe Arg Phe Phe Xaa Xaa
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa = 6-aminohexanoic acid
<220> FEATURE:
<221> NAME/KEY: Xaa
<222> LOCATION: (9)..(9)
<223> OTHER INFORMATION: Xaa = beta-Alanine
<220> FEATURE:
<221> NAME/KEY: VARIANT
<222> LOCATION: (9)..(9)
<223> OTHER INFORMATION: amino acid conjugated to cttcgatagtg nucleotide
      sequence

<400> SEQUENCE: 92

Arg Phe Phe Arg Phe Phe Arg Xaa Xaa
1               5

<210> SEQ ID NO 93
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (2)..(9)
```

```
-continued

<223> OTHER INFORMATION: Xaa = 6-aminohexanoic acid
<220> FEATURE:
<221> NAME/KEY: Xaa
<222> LOCATION: (10)..(10)
<223> OTHER INFORMATION: Xaa = beta-Alanine
<220> FEATURE:
<221> NAME/KEY: VARIANT
<222> LOCATION: (10)..(10)
<223> OTHER INFORMATION: amino acid conjugated to cttcgatagtg nucleotide
      sequence

<400> SEQUENCE: 93

Arg Xaa Xaa Arg Xaa Xaa Arg Xaa Xaa Xaa
1               5                   10

<210> SEQ ID NO 94
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 94
tgctcatact c                                                          11

<210> SEQ ID NO 95
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 95
atagtgctca t                                                          11

<210> SEQ ID NO 96
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 96
gcgttcttcc g                                                          11
```

ANTISENSE ANTIBACTERIAL METHOD AND COMPOUND

CROSS-REFERENCE TO RELATED APPLICATIONS

This application claims the benefit of U.S. Provisional Application No. 60/699,280, filed Jul. 13, 2005, incorporated herein by reference in its entirety.

FIELD OF THE INVENTION

The present invention relates to peptide-conjugated oligonucleotide compounds that are antisense to bacterial genes and methods for use of such compounds in inhibiting bacterial growth, e.g., in an infected mammalian subject.

REFERENCES

Anderson, K. P., M. C. Fox, et al. (1996). *Antimicrob Agents Chemother* 40(9): 2004-11.
Blommers, M. J., U. Pieles, et al. (1994). *Nucleic Acids Res* 22(20): 4187-94.
Bramhill, D. (1997). *Annu Rev Cell Dev Biol* 13: 395-424.
Cross, C. W., J. S. Rice, et al. (1997). *Biochemistry* 36(14): 4096-107.
Donachie, W. D. (1993). *Annu Rev Microbiol* 47: 199-230.
Gait, M. J., A. S. Jones, et al. (1974). *J Chem Soc [Perkin 1]* 0(14): 1684-6.
Geller, B. L., J. D. Deere, et al. (2003). *Antimicrob Agents Chemother* 47(10): 3233-9.
Geller, B. L. and H. M. Green (1989). *J Biol Chem* 264(28): 16465-9.
Gerdes, S. Y., M. D. Scholle, et al. (2003). *J Bacteriol* 185 (19): 5673-84.
Good, L., S. K. Awasthi, et al. (2001). *Nat Biotechnol* 19(4): 360-4.
Good, L. and P. E. Nielsen (1998). *Proc Natl Acad Sci USA* 95(5): 2073-6.
Hale, C. A. and P. A. de Boer (1999). *J Bacteriol* 181(1): 167-76.
Lesnikowski, Z. J., M. Jaworska, et al. (1990). *Nucleic Acids Res* 18(8): 2109-15.
Lutkenhaus, J. and S. G. Addinall (1997). *Annu Rev Biochem* 66: 93-116.
Mertes, M. P. and E. A. Coats (1969). *J Med Chem* 12(1): 154-7.
Pari, G. S., A. K. Field, et al. (1995). *Antimicrob Agents Chemother* 39(5): 1157-61.
Rahman, M. A., J. Summerton, et al. (1991). *Antisense Res Dev* 1(4): 319-27.
Summerton, J., D. Stein, et al. (1997). *Antisense Nucleic Acid Drug Dev* 7(2): 63-70.
Summerton, J. and D. Weller (1997). *Antisense Nucleic Acid Drug Dev* 7(3): 187-95.
Zhang, Y. and J. E. Cronan, Jr. (1996). *J Bacteriol* 178(12): 3614-20.

BACKGROUND OF THE INVENTION

Currently, there are several types of antibiotic compounds in use against bacterial pathogens, and these compounds act through a variety of anti-bacterial mechanisms. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamycin. This class of compounds targets the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNA's with the corresponding mRNA codon. Macrolides and lincosamides, another class of antibiotics, inhibit bacterial synthesis by binding to the 50S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. For those antibiotics that act by inhibiting a bacterial enzyme, such as for sulfonamides, point mutations in the target enzyme may confer resistance.

The appearance of antibiotic resistance in many pathogenic bacteria—in many cases involving multi-drug resistance—has raised the specter of a pre-antibiotic era in which many bacterial pathogens are simply untreatable by medical intervention. There are two main factors that could contribute to this scenario. The first is the rapid spread of resistance and multi-resistance genes across bacterial strains, species, and genera by conjugative elements, the most important of which are self-transmissible plasmids. The second factor is a lack of current research efforts to find new types of antibiotics, due in part to the perceived investment in time and money needed to find new antibiotic agents and bring them through clinical trials, a process that may require a 20-year research effort in some cases.

In addressing the second of these factors, some drug-discovery approaches that may accelerate the search for new antibiotics have been proposed. For example, efforts to screen for and identify new antibiotic compounds by high-throughput screening have been reported, but to date no important lead compounds have been discovered by this route.

Several approaches that involve antisense agents designed to block the expression of bacterial resistance genes or to target cellular RNA targets, such as the rRNA in the 30S ribosomal subunit, have been proposed (Rahman, Summerton et al. 1991; Good and Nielsen 1998). In general, these approaches have been successful only in a limited number of cases, or have required high antisense concentrations (e.g., (Summerton, Stein et al. 1997), or the requirement that the treated cells show high permeability for antibiotics (Good and Nielsen 1998; Geller, Deere et al. 2003).

There is thus a growing need for new antibiotics that (i) are not subject to the principal types of antibiotic resistance currently hampering antibiotic treatment of bacteria, (ii) can be developed rapidly and with some reasonable degree of predictability as to target-bacteria specificity, (iii) can also be designed for broad-spectrum activity, (iv) are effective at low doses, meaning, in part, that they are efficiently taken up by wild-type bacteria or even bacteria that have reduced permeability for antibiotics, and (v) show few side effects.

SUMMARY OF THE INVENTION

The invention includes, in one aspect, an antibacterial antisense conjugate for use in treating a bacterial infection in a mammalian host. The conjugate includes a substantially uncharged antisense oligonucleotide having between 10-20 bases and a targeting sequence of at least 10 contiguous bases complementary to a target region of the infecting bacteria's mRNA for acyl carrier protein (acpP), gyrase A subunit (gyrA), or ftsZ gene, where the target region contains the translational start codon of the bacterial mRNA, or a sequence that is within 20 bases, in a downstream direction, of the translational start codon, and where oligonucleotide binds to the mRNA to form a heteroduplex having a $T_m$ of at least 50°, thereby to inhibit replication of the bacteria.

Also included in the conjugate, and conjugated to the oligonucleotide, is an arginine-rich carrier protein coupled to the oligonucleotide at the peptide's C terminus, and preferably represented by the peptide sequence $(RXX)_n$-, where X is an uncharged amino acid selected from the group consisting of alanine, β-alanine, valine, leucine, isoleucine, serine, threonine, phenyalanine, and tryptophan, and n=2 or 3.

In exemplary embodiments, the carrier peptide has the sequence $(RFF)_n$ or $(RFF)_nR$, where n=2 or 3. The carrier peptide may be linked at its C-terminus to one end of the oligonucleotide, e.g., the 5'-end, through a one- or two-amino acid linker, such as the linker is AhxβAla, where Ahx is 6-aminohexanoic acid and βAla is β-alanine.

The arginine-rich carrier peptide in the conjugate preferably has the ability, when conjugated to the 5' end of a phosphorodiamidate-linked morpholino oligomer (PMO) having SEQ ID NO:66, to enhance the anti-bacterial activity of the PMO by a factor of at least 10, preferably at least $10^2$, as measured by the reduction in bacterial colony-forming units/ ml (CFU/ml) when the peptide-conjugated PMO compound is added at a concentration of 20 μM in a culture to *E coli*, strain W3110 at 5×10$^7$ CFU/ml in Luria broth for a period of 8 hours at 37° C. with aeration, relative to the same activity of the PMO oligonucleotide alone.

The oligonucleotide of the conjugate may be composed of morpholino subunits and phosphorus-containing intersubunit linkages joining a morpholino nitrogen of one subunit to a 5' exocyclic carbon of an adjacent subunit. The morpholino subunits in the oligonucleotide may be joined by phosphorodiamidate linkages, in accordance with the structure:

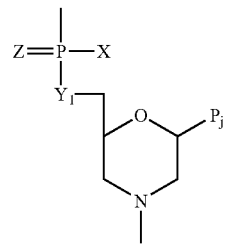

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

The targeting sequence of the oligonucleotide may be complementary to a target sequence containing or within 20 bases, in a downstream direction, of the translational start codon of a bacterial mRNA that encodes acyl carrier protein (acpP). In various embodiments, particularly for use in treating a gram-negative bacterial infection, the targeting sequence may be complementary to at least ten contiguous bases in a sequence selected from the group consisting of SEQ ID NOS: 2, 5, 8, 11, 14, 17, 20, 23, 28, 31, 34, 36, 39, 42, 45, 48, 51, 54, 57 and 60.

Alternatively, the targeting sequence of the oligonucleotide may be complementary to a target sequence containing or within 20 bases, in a downstream direction, of the translational start codon of a bacterial mRNA that encodes gyrase A subunit (gyrA). In various embodiments, particularly for use in treating a gram-negative bacterial infection, the targeting sequence may be complementary to at least ten contiguous bases in a sequence selected from the group consisting of SEQ ID NOS: 3, 6, 9, 12, 15, 18, 24, 29, 32, 35, 37, 40, 43, 46, 49, 52, 55, 58 and 61.

Where, the conjugate targets a bacterial mRNA encoding a bacterial ftsZ protein, the compound targeting sequence may be complementary to at least ten contiguous bases in a sequence selected from the group consisting of SEQ ID NOS: 1, 4, 7, 10, 13, 16, 19, 22, 27, 30, 33, 38, 41, 44, 47, 50, 53, 56 and 59.

In accordance with another aspect of the invention, the conjugate is used in treating a bacterial infection, by administering a therapeutically effective amount of the conjugate to a mammalian host.

These and other objects and features of the claimed subject matter will become more fully apparent when the following detailed description is read in conjunction with the accompanying drawings.

BRIEF DESCRIPTION OF THE FIGURES

FIGS. 2A-2G show examples of uncharged linkage types in oligonucleotide analogs and FIG. 2H shows a cationic linkage group.

DETAILED DESCRIPTION

I. Definitions

Figure 1A:
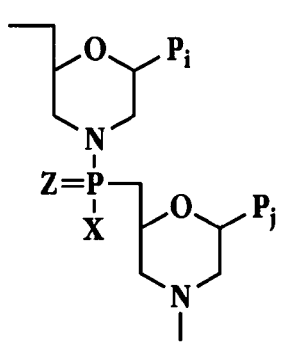
FIGS. 1A-D show the repeating subunit segment of exemplary morpholino oligonucleotides, designated A through D, constructed using subunits having 5-atom (A), six-atom (B) and seven-atom (C-D) linking groups suitable for forming polymers.

The terms below, as used herein, have the following meanings, unless indicated otherwise:

As used herein, the terms "compound", "agent", "oligomer" and "oligonucleotide" may be used interchangeably with respect to the antisense oligonucleotides of the claimed subject matter.

As used herein, the terms "antisense oligonucleotide" and "oligonucleotide" or "antisense compound" or "oligonucleotide compound" are used interchangeably and refer to a sequence of subunits, each having a base carried on a backbone subunit composed of ribose or other pentose sugar or morpholino group, and where the backbone groups are linked by intersubunit linkages (the majority of which are uncharged) that allow the bases in the compound to hybridize to a target sequence in an RNA by Watson-Crick base pairing, to form an RNA:oligonucleotide heteroduplex within the target sequence. The oligonucleotide may have exact sequence complementarity to the target sequence or near complementarity. Such antisense oligonucleotides are designed to block or inhibit translation of the mRNA containing the target sequence, and may be said to be "directed to" a sequence with which it hybridizes. Exemplary structures for antisense oligonucleotides for use in the claimed subject matter include the β-morpholino subunit types shown in FIGS. 1A-D. It will be appreciated that a polymer may contain more than one linkage type.

The term "oligonucleotide" or "antisense oligonucleotide" also encompasses an oligonucleotide having one or more additional moieties conjugated to the oligonucleotide, e.g., at its 3'- or 5'-end, such as a polyethyleneglycol moiety or other hydrophilic polymer, e.g., one having 10-100 monomeric subunits, which may be useful in enhancing solubility, or a moiety such as a lipid or peptide moiety that is effective to enhance the uptake of the compound into target bacterial cells and/or enhance the activity of the compound within the cell, e.g., enhance its binding to a target polynucleotide.

A carrier peptide conjugated to an antisense oligonucleotide, e.g., by covalent linkage between the peptide's C terminal end and the 5' end of the oligonucleotide, is separately named, i.e., not included within the term "oligonucleotide." The carrier peptide and covalently attached antisense oligonucleotide are also referred to herein as a conjugate or conjugate compound. More generally, a "peptide-conjugated morpholino antisense oligonucleotide" is a morpholino antisense oligonucleotide conjugated at either its 5' or 3' termini to an arginine-rich peptide carrier.

By "arginine-rich carrier peptide" is meant that the carrier peptide that has at least 2, and preferably 2-4 arginine residues, each preferably separated by one or more uncharged, hydrophobic residues (at least as hydrophobic as threonine), and preferably containing 6-12 amino acid residues. Exemplary arginine rich peptides are listed as SEQ ID NOS:79-82, and 85-87. In exemplary embodiments, the carrier peptide has the sequence $(RXX)_n$, where X is an uncharged amino acid selected from the group consisting of alanine, β-alanine, valine, leucine, isoleucine, serine, threonine, phenyalanine, and tryptophan, and n=2 or 3. In preferred embodiments, the carrier peptide has the form $(RFF)_n$ or $(RFF)_nR$, where n=2 or 3. The carrier peptide may be linked at its C-terminus to one end of the oligonucleotide, e.g., the 5'-end, through a one- or two-amino acid linker, such as the linker is AhxβAla, where Ahx is 6-aminohexanoic acid and βAla is β-alanine, and where the linker forms part of the carrier peptide.

FIG. 1A shows a 1-atom phosphorous-containing linkage which forms the five atom repeating-unit backbone where the morpholino rings are linked by a 1-atom phosphonamide linkage.

Figure 1B:
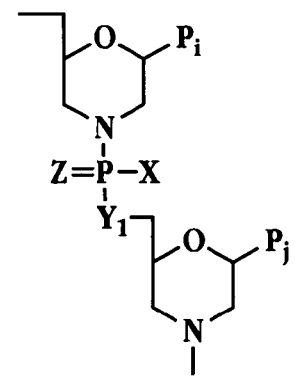

FIG. 1B shows a six atom repeating-unit backbone where the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures.

Figure 1C:
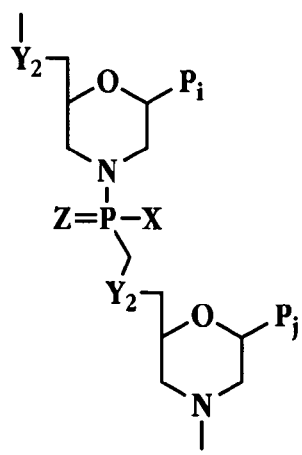
Figure 1D:
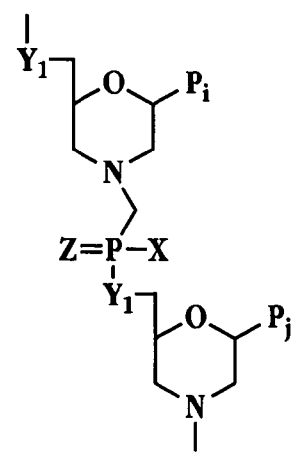

FIGS. 1C-D show 7-atom unit-length backbones. In FIG. 1C the X moiety is as in Structure B of FIG. 1 and the moiety Y may be a methylene, sulfur, or preferably oxygen. In the structure shown in FIG. 1D the X and Y moieties are as in FIG. 1B. In all subunits depicted in FIGS. 1A-D, Z is O or S, and $P_i$ or $P_j$ is adenine, cytosine, guanine, thymine, uracil or inosine.

As used herein, a "morpholino oligomer" or "morpholino oligonucleotide" refers to an antisense oligonucleotide having a backbone which supports bases capable of hydrogen bonding to natural polynucleotides, e.g., DNA or RNA, is composed of morpholino subunit structures of the form shown in FIG. 1B, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide.

This preferred aspect of the claimed subject matter is illustrated in FIG. 2G, which shows two such subunits joined by a phosphorodiamidate linkage. Morpholino oligonucleotides (including antisense oligonucleotides) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein. FIG. 2H shows a cationic linkage group.

As used herein, a "nuclease-resistant" oligonucleotide molecule (oligonucleotide) is one whose backbone is not susceptible to nuclease cleavage of a phosphodiester bond. Exemplary nuclease resistant antisense oligonucleotides are oligonucleotide analogs, such as phosphorothioate and phosphate-amine DNA (pnDNA), both of which have a charged backbone, and methyl-phosphonate, and morpholino oligonucleotides, all of which may have uncharged backbones.

As used herein, an antisense oligonucleotide "specifically hybridizes" to a target polynucleotide if the oligonucleotide hybridizes to the target under physiological conditions, with a Tm greater than 37° C. As will be seen below, the antisense oligonucleotides of the claimed subject matter have a preferred Tm values with respect to their target mRNAs of at least 50° C., typically between 50°-60° C. or greater.

The "Tm" of an oligonucleotide compound, with respect to its target mRNA, is the temperature at which 50% of a target sequence hybridizes to a complementary polynucleotide. Tm is determined under standard conditions in physiological saline, as described, for example, in Miyada C. G. and Wallace R. B. 1987, Oligonucleotide hybridization techniques, *Methods Enzymol.*, 154:94-107.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein, a first sequence is an "antisense sequence" with respect to a second sequence if a polynucleotide whose sequence is the first sequence specifically binds to, or specifically hybridizes with, the second polynucleotide sequence under physiological conditions.

As used herein, a "base-specific intracellular binding event involving a target RNA" refers to the sequence specific binding of an oligonucleotide to a target RNA sequence inside a cell. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligonucleotide to its complementary target, which is resistant to in vivo degradation by ubiquitous intracellular and extracellular nucleases.

As used herein, "essential bacterial genes" are those genes whose products play an essential role in an organism's functional repertoire as determined using genetic footprinting or other comparable techniques to identify gene essentiality.

An agent is "actively taken up by bacterial cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide compound preferably has a substantially uncharged backbone, as defined below.

As used herein, the terms "modulating expression" and "antisense activity" relative to an oligonucleotide refers to the ability of an antisense oligonucleotide to either enhance or reduce the expression of a given protein by interfering with the expression, or translation of RNA. In the case of reduced protein expression, the antisense oligonucleotide may directly block expression of a given gene, or contribute to the accelerated breakdown of the RNA transcribed from that gene.

As used herein, the term "inhibiting bacterial growth, refers to blocking or inhibiting replication and/or reducing the rate of replication of bacterial cells in a given environment, for example, in an infective mammalian host.

As used herein, the term "pathogenic bacterium," or "pathogenic bacteria," or "pathogenic bacterial cells," refers to bacterial cells capable of infecting and causing disease in a mammalian host, as well as producing infection-related symptoms in the infected host, such as fever or other signs of inflammation, intestinal symptoms, respiratory symptoms, dehydration, and the like.

As used herein, the terms "Gram-negative pathogenic bacteria" or "Gram-negative bacteria" refer to the phylum of proteobacteria, which have an outer membrane composed largely of lipopolysaccharides. All proteobacteria are gram negative, and include, but are not limited to *Escherichia coli*, *Salmonella*, other *Enterobacteriaceae*, *Pseudomonas*, *Burkholderi*, *Moraxella*, *Helicobacter*, *Stenotrophomonas*, *Bdellovibrio*, acetic acid bacteria, and *Legionella*. Other notable groups of gram negative bacteria include *Haemophilus influenzae*, the cyanobacteria, spirochaetes, green sulfur and green non-sulfur bacteria. The pathogenic capability of gram negative bacteria is usually associated with components of the bacterial cell wall, in particular the lipopolysaccharide (also known as LPS or endotoxin) layer.

As used herein, the terms "Gram-positive pathogenic bacteria" or "Gram-positive bacteria" refer to those bacteria that are stained dark blue or violet by Gram staining, in contrast to Gram-negative bacteria, which cannot retain the stain, instead taking up the counterstain and appearing red or pink. The stain is caused by a high amount of peptidoglycan in the cell wall, which typically, but not always, lacks the secondary membrane and lipopolysaccharide layer found in Gram-negative bacteria.

Gram-positive bacteria include many well-known genera such as *Bacillus*, *Listeria*, *Staphylococcus*, *Streptococcus*, *Enterococcus*, and *Clostridium*. It has also been expanded to include the *Mollicutes*, and bacteria such as *Mycoplasma*, which lack cell walls and so cannot be stained by Gram, but are derived from such forms.

As used herein, "effective amount" or "therapeutically effective amount" or "growth-inhibiting amount" relative to an antisense oligonucleotide refers to the amount of antisense oligonucleotide administered to a mammalian subject, either as a single dose or as part of a series of doses and which is effective to inhibit bacterial replication in an infected host, by inhibiting translation of a selected bacterial target nucleic acid sequence. The ability to block or inhibit bacterial replication in an infected host may be evidenced by a reduction in infection-related symptoms.

As used herein "treatment" of an individual or a cell is any type of intervention used in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent.

A "substantially uncharged", phosphorus containing backbone in an oligonucleotide analog is one in which a majority of the subunit linkages, e.g., between 50-100%, are uncharged at physiological pH, and contain a single phosphorous atom, For example, the backbone may contain only uncharged linkages or 1 positively charged linkage per every 3-10 linkages.

II. Exemplary Oligonucleotide Backbones

Examples of nonionic linkages that may be used in oligonucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine, thymidine, uracil and inosine. Suitable backbone structures include carbonate (2A, R=O) and carbamate (2A, R=NH$_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Blommers, Pieles et al. 1994); sulfone and sulfonamide linkages (2D, R1, R2=CH$_2$); and a thioformacetyl linkage (2E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 2F. The structure shown in FIG. 2H is an exemplary cationic linkage type.

A preferred oligonucleotide structure employs morpholino-based subunits bearing base-pairing moieties as illustrated in FIGS. 1A-1D, joined by uncharged linkages, as described above. Especially preferred is a substantially uncharged phosphorodiamidate-linked morpholino oligonucleotide, such as illustrated in FIG. 2G. Morpholino oligonucleotides, including antisense oligonucleotides, are detailed, for example, in (Summerton and Weller 1997) and in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: 1) the ability to be linked in a oligomeric form by stable, uncharged backbone linkages; 2) the ability to support a nucleotide base (e.g. adenine, cytosine, guanine, thymidine, uracil and inosine) such that the polymer formed can hybridize with a complementary-base target nucleic acid, including target RNA, Tm values above about 50° C. in relatively short oligonucleotides (e.g., 10-15 bases); 3) the ability of the oligonucleotide to be actively or passively transported into bacterial cells; and 4) the ability of the oligonucleotide:RNA heteroduplex to resist RNAse degradation.

A. Exemplary Antisense Oligonucleotides

Exemplary backbone structures for antisense oligonucleotides of the claimed subject matter include the β-morpholino subunit types shown in FIGS. 1A-1D, each linked by an uncharged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

The linkages shown in FIG. 1C and 1D are designed for 7-atom unit-length backbones. In Structure 1C, the X moiety is as in Structure 1B, and the moiety Y may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where X=NH$_2$ or N(CH$_3$)$_2$, Y=O, and Z=O.

As noted above, the substantially uncharged oligonucleotide may include a one or more of charged linkages, e.g. up to about 1 per every 3-10 uncharged linkages, such as about 1 per every 10 uncharged linkages. Therefore, a small number of charged linkages, e.g. charged phosphoramidate or phosphorothioate, may also be incorporated into the oligomers. An exemplary cationic linkage is shown in FIG. 2H.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

B. Antibacterial Antisense Oligonucleotides

In addition to the structural features described above, the antisense compound of the claimed subject matter contains no more than 20 nucleotide bases, and has a targeting nucleic acid sequence (the sequence which is complementary to the target sequence) of no fewer than 10 contiguous bases. The targeting sequence is complementary to a target sequence containing or within 15 bases, in a downstream direction, of the translational start codon of a bacterial mRNA that encodes a bacterial protein essential for bacterial replication. The compound has a $T_m$, when hybridized with the target sequence, of at least about 50° C., typically between about 50° to 60° C., although the Tm may be higher, e.g., 65° C. The selection of bacterial targets, and bacterial mRNA target sequences and complementary targeting sequences are considered in the two sections below.

The antisense compound is covalently conjugated to an 8 to 12 residue arginine-rich peptide at either the 5' or 3' end of the antisense oligomer of the type described above.

III. Bacterial Targets

This section considers a number of bacterial targets, including pathogenic bacteria, and specific bacterial protein targets against which the antisense compound can be directed.

A. Bacterial Targets

*Escherichia coil* (*E. coli*) is a Gram-negative bacterium that is part of the normal flora of the gastrointestinal tract. There are hundreds of strains of *E. coli*, most of which are harmless and live in the gastrointestinal tract of healthy humans and animals. Currently, there are four recognized classes of enterovirulent *E. coli* (the "EEC group") that cause gastroenteritis in humans. Among these are the enteropathogenic (EPEC) strains and those whose virulence mechanism is related to the excretion of typical *E. coli* enterotoxins. Such strains of *E. coli* can cause various diseases including those associated with infection of the gastrointestinal tract and urinary tract, septicemia, pneumonia, and meningitis. Antibiotics are not effective against some strains and do not necessarily prevent recurrence of infection.

For example, *E. coli* strain 0157:H7 is estimated to cause 10,000 to 20,000 cases of infection in the United States annually (Federal Centers for Disease Control and Prevention). Hemorrhagic colitis is the name of the acute disease caused by *E. coli* O157:H7. Preschool children and the elderly are at the greatest risk of serious complications. *E. coli* strain 0157: H7 was recently reported as the cause the death of four children who ate under cooked hamburgers from a fast-food restaurant in the Pacific Northwest. (See, e.g., Jackson et al., *Epidemiol. Infect.* 120 (1):17-20, 1998.)

Exemplary sequences for enterovirulent *E. coli* strains include GenBank Accession Numbers AB011549, X97542, AF074613, Y11275 and AJ007716.

*Salmonella thyohimurium*, are Gram-negative bacteria which cause various conditions that range clinically from localized gastrointestinal infections, gastroenterits (diarrhea, abdominal cramps, and fever) to enteric fevers (including typhoid fever) which are serious systemic illnesses. *Salmonella* infection also causes substantial losses of livestock.

Typical of Gram-negative bacilli, the cell wall of *Salmonella* spp. contains a complex lipopolysaccharide (LPS) structure that is liberated upon lysis of the cell and may function as an endotoxin, which contributes to the virulence of the organism.

Contaminated food is the major mode of transmission for non-typhoidal *salmonella* infection, due to the fact that *Salmonella* survive in meats and animal products that are not thoroughly cooked. The most common animal sources are chickens, turkeys, pigs, and cows; in addition to numerous other domestic and wild animals. The epidemiology of typhoid fever and other enteric fevers caused by *Salmonella* spp. is associated with water contaminated with human feces.

Vaccines are available for typhoid fever and are partially effective; however, no vaccines are available for non-typhoidal *Salmonella* infection. Non-typhoidal salmonellosis is controlled by hygienic slaughtering practices and thorough cooking and refrigeration of food. Antibiotics are indicated for systemic disease, and Ampicillin has been used with some success. However, in patients under treatment with excessive amounts of antibiotics, patients under treatment with immunsuppressive drugs, following gastric surgery, and in patients with hemolytic anemia, leukemia, lymphoma, or AIDS, *Salmonella* infection remains a medical problem.

*Pseudomonas* spp. are motile, Gram-negative rods which are clinically important because they are resistant to most antibiotics, and are a major cause of hospital acquired (nosocomial) infections. Infection is most common in: immunocompromised individuals, burn victims, individuals on respirators, individuals with indwelling catheters, IV narcotic users and individual with chronic pulmonary disease (e.g., cystic fibrosis). Although infection is rare in healthy individuals, it can occur at many sites and lead to urinary tract infections, sepsis, pneumonia, pharyngitis, and numerous other problems, and treatment often fails with greater significant mortality.

*Pseudomonas aeruginosa* is a Gram-negative, aerobic, rod-shaped bacterium with unipolar motility. An opportunistic human pathogen, *P. aeruginosa* is also an opportunistic pathogen of plants. Like other *Pseudomonads*, *P. aeruginosa* secretes a variety of pigments. Definitive clinical identification of *P. aeruginosa* can include identifying the production of both pyocyanin and fluorescein as well as the organism's ability to grow at 42° C. *P. aeruginosa* is also capable of growth in diesel and jet fuel, for which it is known as a hydrocarbon utilizing microorganism (or "HUM bug"), causing microbial corrosion.

*Vibrio cholera* is a Gram-negative rod which infects humans and causes cholera, a disease spread by poor sanitation, resulting in contaminated water supplies. *Vibrio cholerae* can colonize the human small intestine, where it produces a toxin that disrupts ion transport across the mucosa, causing diarrhea and water loss. Individuals infected with *Vibrio cholerae* require rehydration either intravenously or orally with a solution containing electrolytes. The illness is generally self-limiting; however, death can occur from dehydration and loss of essential electrolytes. Antibiotics such as tetracycline have been demonstrated to shorten the course of the illness, and oral vaccines are currently under development.

*Neisseria gonorrhoea* is a Gram-negative coccus, which is the causative agent of the common sexually transmitted disease, gonorrhea. *Neisseria gonorrhoea* can vary its surface antigens, preventing development of immunity to reinfection. Nearly 750,000 cases of gonorrhea are reported annually in the United States, with an estimated 750,000 additional unreported cases annually, mostly among teenagers and young adults. Ampicillin, amoxicillin, or some type of penicillin used to be recommended for the treatment of gonorrhea. However, the incidence of penicillin-resistant gonorrhea is increasing, and new antibiotics given by injection, e.g., ceftriaxone or spectinomycin, are now used to treat most gonococcal infections.

*Staphylococcus aureus* is a Gram-positive coccus which normally colonizes the human nose and is sometimes found on the skin. *Staphylococcus* can cause bloodstream infections, pneumonia, and surgical-site infections in the hospital setting (i.e., nosocomial infections). *Staph. aureus* can cause severe food poisoning, and many strains grow in food and produce exotoxins. *Staphylococcus* resistance to common antibiotics, e.g., vancomycin, has emerged in the United States and abroad as a major public health challenge both in community and hospital settings. Recently, a vancomycin-resistant *Staph. aureus* isolate has also been identified in Japan.

*Mycobacterium tuberculosis* is a Gram positive bacterium which is the causative agent of tuberculosis, a sometimes crippling and deadly disease. Tuberculosis is on the rise and globally and the leading cause of death from a single infectious disease (with a current death rate of three million people per year). It can affect several organs of the human body, including the brain, the kidneys and the bones, however, tuberculosis most commonly affects the lungs.

In the United States, approximately ten million individuals are infected with *Mycobacterium tuberculosis*, as indicated by positive skin tests, with approximately 26,000 new cases of active disease each year. The increase in tuberculosis (TB) cases has been associated with HIV/AIDS, homelessness, drug abuse and immigration of persons with active infections. Current treatment programs for drug-susceptible TB involve taking two or four drugs (e.g., isoniazid, rifampin, pyrazinamide, ethambutol or streptomycin), for a period of from six to nine months, because all of the TB germs cannot be destroyed by a single drug. In addition, the observation of drug-resistant and multiple drug resistant strains of *Mycobacterium tuberculosis* is on the rise.

*Helicobacter pylori* (*H. pylori*) is a micro-aerophilic, Gram-negative, slow-growing, flagellated organism with a spiral or S-shaped morphology which infects the lining of the stomach. *H. pylori* is a human gastric pathogen associated with chronic superficial gastritis, peptic ulcer disease, and chronic atrophic gastritis leading to gastric adenocarcinoma. *H. pylori* is one of the most common chronic bacterial infections in humans and is found in over 90% of patients with active gastritis. Current treatment includes triple drug therapy with bismuth, metronidazole, and either tetracycline or amoxicillin which eradicates *H. pylori* in most cases. Problems with triple therapy include patient compliance, side effects, and metronidazole resistance. Alternate regimens of dual therapy which show promise are amoxicillin plus metronidazole or omeprazole plus amoxicillin.

*Streptococcus pneumoniae* is a Gram-positive coccus and one of the most common causes of bacterial pneumonia as well as middle ear infections (otitis media) and meningitis. Each year in the United States, pneumococcal diseases account for approximately 50,000 cases of bacteremia; 3,000 cases of meningitis; 100,000-135,000 hospitalizations; and 7 million cases of otitis media. Pneumococcal infections cause an estimated 40,000 deaths annually in the United States. Children less than 2 years of age, adults over 65 years of age and persons of any age with underlying medical conditions, including, e.g., congestive heart disease, diabetes, emphysema, liver disease, sickle cell, HIV, and those living in special environments, e.g., nursing homes and long-term care facilities, at highest risk for infection.

Drug-resistant *S. pneumoniae* strains have become common in the United States, with many penicillin-resistant pneumococci also resistant to other antimicrobial drugs, such as erythromycin or trimethoprim-sulfamethoxazole.

*Treponema pallidum* is a spirochete which causes syphilis. *T. pallidum* is exclusively a pathogen which causes syphilis, yaws and non-venereal endemic syphilis or pinta. *Treponema pallidum* cannot be grown in vitro and does replicate in the absence of mammalian cells. The initial infection causes an ulcer at the site of infection; however, the bacteria move throughout the body, damaging many organs over time. In its late stages, untreated syphilis, although not contagious, can cause serious heart abnormalities, mental disorders, blindness, other neurologic problems, and death.

Syphilis is usually treated with penicillin, administered by injection. Other antibiotics are available for patients allergic to penicillin, or who do not respond to the usual doses of penicillin. In all stages of syphilis, proper treatment will cure the disease, but in late syphilis, damage already done to body organs cannot be reversed.

*Chlamydia trachomatis* is the most common bacterial sexually transmitted disease in the United States and it is estimated that 4 million new cases occur each year. The highest rates of infection are in 15 to 19 year olds. *Chlamydia* is a major cause of non-gonococcal urethritis (NGU), cervicitis, bacterial vaginitis, and pelvic inflammatory disease (PID). *Chlamydia* infections may have very mild symptoms or no symptoms at all; however, if left untreated *Chlamydia* infections can lead to serious damage to the reproductive organs, particularly in women. Antibiotics such as azithromycin, erythromycin, ofloxacin, amoxicillin or doxycycline are typically prescribed to treat *Chlamydia* infection.

*Bartonella henselae* Cat Scratch Fever (CSF) or cat scratch disease (CSD), is a disease of humans acquired through exposure to cats, caused by a Gram-negative rod originally named *Rochalimaea henselae*, and currently known as *Bartonella henselae*. Symptoms include fever and swollen lymph nodes and CSF is generally a relatively benign, self-limiting disease in people, however, infection with *Bartonella henselae* can produce distinct clinical symptoms in immunocompromised people, including, acute febrile illness with bacteremia, bacillary angiomatosis, peliosis hepatis, bacillary splenitis, and other chronic disease manifestations such as AIDS encephalopathy.

The disease is treated with antibiotics, such as doxycycline, erythromycin, rifampin, penicillin, gentamycin, ceftriaxone, ciprofloxacin, and azithromycin.

*Haemophilus influenzae* (*H. influenza*) is a family of Gram-negative bacteria; six types of which are known, with most *H. influenza*-related disease caused by type B, or "HIB". Until a vaccine for HIB was developed, HIB was a common causes of otitis media, sinus infections, bronchitis, the most common cause of meningitis, and a frequent culprit in cases of pneumonia, septic arthritis (joint infections), cellulitis (infections of soft tissues), and pericarditis (infections of the membrane surrounding the heart). The *H. influenza* type B bacterium is widespread in humans and usually lives in the throat and nose without causing illness. Unvaccinated children under age 5 are at risk for HIB disease. Meningitis and other serious infections caused by *H. influenza* infection can lead to brain damage or death.

*Shigella dysenteriae* (*Shigella dys.*) is a Gram-negative rod which causes dysentary. In the colon, the bacteria enter mucosal cells and divide within mucosal cells, resulting in an extensive inflammatory response. *Shigella* infection can cause severe diarrhea which may lead to dehydration and can be dangerous for the very young, very old or chronically ill. *Shigella dys.* forms a potent toxin (shiga toxin), which is cytotoxic, enterotoxic, neurotoxic and acts as a inhibitor of protein synthesis. Resistance to antibiotics such as ampicillin and TMP-SMX has developed, however, treatment with newer, more expensive antibiotics such as ciprofloxacin, norfloxacin and enoxacin, remains effective.

*Listeria* is a genus of Gram-positive, motile bacteria found in human and animal feces. *Listeria monocytogenes* causes such diseases as listeriosis, meningoencephalitis and meningitis. This organism is one of the leading causes of death from food-borne pathogens especially in pregnant women, newborns, the elderly, and immunocompromised individuals. It is found in environments such as decaying vegetable matter, sewage, water, and soil, and it can survive extremes of both temperatures and salt concentration making it an extremely dangerous food-born pathogen, especially on food that is not reheated. The bacterium can spread from the site of infection in the intestines to the central nervous system and the fetal-placental unit. Meningitis, gastroenteritis, and septicemia can result from infection. In cattle and sheep, *listeria* infection causes encephalitis and spontaneous abortion.

*Proteus mirabilis* is an enteric, Gram-negative commensal organism, distantly related to *E. coli*. It normally colonizes the human urethra, but is an opportunistic pathogen that is the leading cause of urinary tract infections in catheterized individuals. *P. mirabilis* has two exceptional characteristics: 1) it has very rapid motility, which manifests itself as a swarming phenomenon on culture plates; and 2) it produce urease, which gives it the ability to degrade urea and survive in the genitourinary tract.

*Yersinia pestis* is the causative agent of plague (bubonic and pulmonary) a devastating disease which has killed millions worldwide. The organism can be transmitted from rats to humans through the bite of an infected flea or from human-to-human through the air during widespread infection. *Yersinia pestis* is an extremely pathogenic organism that requires very few numbers in order to cause disease, and is often lethal if left untreated. The organism is enteroinvasive, and can survive and propagate in macrophages prior to spreading systemically throughout the host.

*Bacillus anthracis* is also known as anthrax. Humans become infected when they come into contact with a contaminated animal. Anthrax is not transmitted due to person-to-person contact. The three forms of the disease reflect the sites of infection which include cutaneous (skin), pulmonary (lung), and intestinal. Pulmonary and intestinal infections are often fatal if left untreated. Spores are taken up by macrophages and become internalized into phagolysozomes (membranous compartment) whereupon germination initiates. Bacteria are released into the bloodstream once the infected macrophage lyses whereupon they rapidly multiply, spreading throughout the circulatory and lymphatic systems, a process that results in septic shock, respiratory distress and organ failure. The spores of this pathogen have been used as a terror weapon.

*Burkholderia mallei* is a Gram-negative aerobic bacterium that causes Glanders, an infectious disease that occurs primarily in horses, mules, and donkeys. It is rarely associated with human infection and is more commonly seen in domesticated animals. This organism is similar to *B. pseudomallei* and is differentiated by being nonmotile. The pathogen is host-adapted and is not found in the environment outside of its host. Glanders is often fatal if not treated with antibiotics, and transmission can occur through the air, or more commonly when in contact with infected animals. Rapid-onset pneumonia, bacteremia (spread of the organism through the blood), pustules, and death are common outcomes during infection. The virulence mechanisms are not well understood, although a type III secretion system similar to the one from *Salmonella typhimurium* is necessary. No vaccine exists for this potentially dangerous organism which is thought to have potential as a biological terror agent. The genome of this organism carries a large number of insertion sequences as compared to the related *Bukholderia pseudomallei* (below), and a large number of simple sequence repeats that may function in antigenic variation of cell surface proteins.

*Burkholderia pseudomallei* is a Gram-negative bacterium that causes meliodosis in humans and animals. Meliodosis is a disease found in certain parts of Asia, Thailand, and Australia. *B. pseudomallei* is typically a soil organism and has been recovered from rice paddies and moist tropical soil, but as an opportunistic pathogen can cause disease in susceptible individuals such as those that suffer from diabetes mellitus. The organism can exist intracellularly, and causes pneumonia and bacteremia (spread of the bacterium through the bloodstream). The latency period can be extremely long, with infection preceding disease by decades, and treatment can take months of antibiotic use, with relapse a commonly observed phenomenon. Intercellular spread can occur via induction of actin polymerization at one pole of the cell, allowing movement through the cytoplasm and from cell-to-cell. This organism carries a number of small sequence repeats which may promoter antigenic variation, similar to what was found with the *B. mallei* genome.

*Burkholderia cepacia* is a Gram-negative bacterium composed of at least seven different sub-species, including *Burkholderia multivorans, Burkholderia vietnamiensis, Burkholderia stabilis, Burkholderia cenocepacia* and *Burkholderia ambifaria*. *B. cepacia* is an important human pathogen which most often causes pneumonia in people with underlying lung disease (such as cystic fibrosis or immune problems (such as (chronic granulomatous disease). *B. cepacia* is typically found in water and soil and can survive for prolonged periods in moist environments. Person-to-person spread has been documented; as a result, many hospitals, clinics, and camps for patients with cystic fibrosis have enacted strict isolation precautions *B. cepacia*. Individuals with the bacteria are often treated in a separate area than those without to limit spread. This is because infection with *B. cepacia* can lead to a rapid decline in lung function resulting in death. Diagnosis of *B. cepacia* involves isolation of the bacteria from sputum cultures. Treatment is difficult because *B. cepacia* is naturally resistant to many common antibiotics including aminoglycosides (such as tobramycin) and polymixin B. Treatment typically includes multiple antibiotics and may include ceftazidime, doxycycline, piperacillin, chloramphenicol, and co-trimoxazole.

*Francisella tularensis* was first noticed as the causative agent of a plague-like illness that affected squirrels in Tulare County in California in the early part of the 20th century by Edward Francis. The organism now bears his namesake. The disease is called tularemia and has been noted throughout recorded history. The organism can be transmitted from infected ticks or deerflies to a human, through infected meat, or via aerosol, and thus is a potential bioterrorism agent. It is an aquatic organism, and can be found living inside protozoans, similar to what is observed with Legionella. It has a high infectivity rate, and can invade phagocytic and nonphagocytic cells, multiplying rapidly. Once within a macrophage, the organism can escape the phagosome and live in the cytosol.

Veterinary Applications

A healthy microflora in the gastrointestinal tract of livestock is of vital importance for health and corresponding production of associated food products. As with humans, the gastrointestinal tract of a healthy animal contains numerous types of bacteria (i.e., *E. coli, Pseudomonas aeruginosa* and *Salmonella* spp.), which live in ecological balance with one another. This balance may be disturbed by a change in diet, stress, or in response to antibiotic or other therapeutic treatment, resulting in bacterial diseases in the animals generally caused by bacteria such as *Salmonella, Campylobacter, Enterococci, Tularemia* and *E. coli*. Bacterial infection in these animals often necessitates therapeutic intervention, which has treatment costs as well being frequently associated with a decrease in productivity.

As a result, livestock are routinely treated with antibiotics to maintain the balance of flora in the gastrointestinal tract.

The disadvantages of this approach are the development of antibiotic resistant bacteria and the carry over of such antibiotics and the resistant bacteria into resulting food products for human consumption.

B. Cell Division and Cell Cycle Target Proteins

The antisense oligomers of the claimed subject matter are designed to hybridize to a region of a bacterial mRNA that encodes an essential bacterial gene. Exemplary genes are those required for cell division, cell cycle proteins, or genes required for lipid biosynthesis or nucleic acid replication. Any essential bacterial gene can be targeted once a gene's essentiality is determined. One approach to determining which genes in an organism are essential is to use genetic footprinting techniques as described (Gerdes, Scholle et al. 2003). In this report, 620 *E. coli* genes were identified as essential and 3,126 genes as dispensable for growth under culture conditions for robust aerobic growth. Evolutionary context analysis demonstrated that a significant number of essential *E. coli* genes are preserved throughout the bacterial kingdom, especially the subset of genes for key cellular processes such as DNA replication, cell division and protein synthesis.

In various aspects, the claimed subject matter provides an antisense oligomer which is a nucleic acid sequence effective to stably and specifically bind to a nucleic acid target sequence which encodes an essential bacterial protein including the following: (1) a sequence specific to a particular strain of a given species of bacteria, such as a strain of *E. coli* associated with food poisoning, e.g., O157:H7 (see Table 1 below); (2) a sequence common to two or more species of bacteria; (3) a sequence common to two related genera of bacteria (i.e., bacterial genera of similar phylogenetic origin); (4) a sequence generally conserved among Gram-negative bacteria; (5) generally conserved among Gram-positive bacteria; or (6) a consensus sequence for essential bacterial protein-encoding nucleic acid sequences in general.

In general, the target for modulation of gene expression using the antisense methods of the claimed subject matter comprises an mRNA expressed during active bacterial growth or replication, such as an mRNA sequence transcribed from a gene of the cell division and cell wall synthesis (dcw) gene cluster, including, but not limited to, zipA, sulA, seca, dicA, dicB, dicC, dicF, ftsA, ftsI, ftsN, ftsK, ftsL, ftsQ, ftsW, ftsZ, murC, murD, murE, murF, murG, minC, minD, minE, mraY, mraW, mraZ, seqA and ddB. See (Bramhill 1997), and (Donachie 1993), both of which are expressly incorporated by reference herein, for general reviews of bacterial cell division and the cell cycle of *E. coli*, respectively. Additional targets include genes involved in lipid biosynthesis (e.g. acpP) and replication (e.g. gyrA).

Cell division in *E. coli* involves coordinated invagination of all 3 layers of the cell envelope (cytoplasmic membrane, rigid peptidoglycan layer and outer membrane). Constriction of the septum severs the cell into 2 compartments and segregates the replicated DNA. At least 9 essential gene products participate in this process: ftsZ, ftsA, ftsQ, ftsL, ftsI, ftsN, ftsK, ftsW and zipA (Hale and de Boer 1999). Preferred protein targets are the three discussed below, and in particular, the GyrA and AcpP targets described below.

FtsZ, one of the earliest essential cell division genes in *E. coli*, is a soluble, tubulin-like GTPase that forms a membrane-associated ring at the division site of bacterial cells. The ring is thought to drive cell constriction, and appears to affect cell wall invagination. FtsZ binds directly to a novel integral inner membrane protein in *E. coli* called zipA, an essential component of the septal ring structure that mediates cell division in *E. coli* (Lutkenhaus and Addinall 1997).

GyrA refers to subunit A of the bacterial gyrase enzyme, and the gene therefore. Bacterial gyrase is one of the bacterial DNA topoisomerases that control the level of supercoiling of DNA in cells and is required for DNA replication.

AcpP encodes acyl carrier protein, an essential cofactor in lipid biosynthesis. The fatty acid biosynthetic pathway requires that the heat stable cofactor acyl carrier protein binds intermediates in the pathway.

For each of these three proteins, Table 1 provides exemplary bacterial sequences which contain a target sequence for each of a number of important pathogenic bacteria. The gene sequences are derived from the GenBank Reference full genome sequence for each bacterial strain (http://www.ncbi.nlm.nih.gov/genomes/lproks.cgi). The gene location on either the positive (+) or negative (−) strand of the genome is listed under "Strand", it being recognized that the strand indicated is the coding sequence for the protein, that is, the sequence corresponding to the mRNA target sequence for that gene. For example, the two *E. coli* genes (ftsZ and acpP) in which the coding sequence is on the positive strand, the sequence is read 5' to 3' in the left-to-right direction. Similarly for the *E. coli* gyrA gene having the coding region on the minus genomic strand, the coding sequence is read as the reverse complement in the right to left direction (5' to 3').

TABLE 1

Exemplary Bacterial Target Gene Sequences

| Organism | GenBank Ref. | Target Gene | Strand | Nucleotide Region |
|---|---|---|---|---|
| Escherichia coli | NC 000913 | ftsZ | + | 105305-106456 |
|  |  | acpP | + | 1150838-1151074 |
|  |  | gyrA | − | 2334813-2337440 |
| Escherichia coli O157:H7 | NC 002655 | ftsZ | + | 109911-111062 |
|  |  | acpP | + | 1595796-1596032 |
|  |  | gyrA | − | 3133832-3136459 |
| Salmonella thyphimurium | NC 003197 | ftsZ | + | 155683-156834 |
|  |  | acpP | + | 1280113-1280349 |
|  |  | gyrA | − | 2373711-2376347 |
| Pseudomonas aeruginosa | NC 002516 | ftsZ | − | 4939299-4940483 |
|  |  | acpP | − | 3324946-3325182 |
|  |  | gyrA | − | 3556426-3559197 |
| Vibrio cholera | NC 002505 | ftsZ | − | 2565047-2566243 |
|  |  | acpP | + | 254505-254747 |
|  |  | gyrA | + | 1330207-1332891 |
| Neisseria gonorrhoea | NC 002946 | ftsZ | − | 1498872-1500050 |
|  |  | acpP | + | 1724401-1724637 |
|  |  | gyrA | − | 618439-621189 |
| Staphylococcus aureus | NC 002745 | ftsZ | + | 1165782-1166954 |
|  |  | gyrA | + | 7005-9674 |
|  |  | fmhB | − | 2321156-2322421 |
| Mycobacterium tuberculosis | NC 002755 | ftsZ | − | 2407076-2408281 |
|  |  | acpP | + | 1510182-1510502 |
|  |  | gyrA | + | 7302-9818 |
|  |  | pimA | − | 2934009-2935145 |
|  |  | cysS2 | − | 4014534-4015943 |
| Helicobacter pylori | NC 000915 | ftsZ | + | 1042237-1043394 |
|  |  | acpP | − | 594037-594273 |
|  |  | gyrA | + | 752512-754995 |
| Streptococcus pneumoniae | NC 003028 | ftsZ | − | 1565447-1566706 |
|  |  | acp | + | 396691-396915 |
|  |  | gyrA | − | 1147387-1149855 |
| Treponema palladium | NC 000919 | ftsZ | + | 414751-416007 |
|  |  | acp | + | 877632-877868 |
|  |  | gyrA | + | 4391-6832 |
| Chlamydia trachomatis | NC 000117 | acpP | − | 263702-263935 |
|  |  | gyrA | − | 755022-756494 |
| Bartonella henselae | NC 005956 | ftsZ | − | 1232094-1233839 |
|  |  | acpP | + | 623143-623379 |
|  |  | gyrA | − | 1120562-1123357 |
| Hemophilis influenza | NC 000907 | ftsZ | + | 1212021-1213286 |
|  |  | acpP | − | 170930-171160 |
|  |  | gyrA | − | 1341719-1344361 |

TABLE 1-continued

Exemplary Bacterial Target Gene Sequences

| Organism | GenBank Ref. | Target Gene | Strand | Nucleotide Region |
|---|---|---|---|---|
| Listeria monocytogenes | NC 002973 | ftsZ | − | 2102307-2101132 |
| | | acpP | − | 1860771-1860538 |
| | | gyrA | + | 8065-10593 |
| Yersinia pestis | NC 003143 | ftsZ | + | 605874-607025 |
| | | acpP | + | 1824120-1824356 |
| | | gyrA | + | 1370729-1373404 |
| Bacillus anthracis | NC 005945 | ftsZ | − | 3724197-3725357 |
| | | acpP | − | 3666663-3666896 |
| | | gyrA | + | 6596-9067 |
| Burkholderia mallei | NC 006348 | ftsZ | − | 2649616-2650812 |
| | | acpP | + | 559430-559669 |
| | | gyrA | − | 459302-461902 |
| Burkholderia pseudomallei | NC 006350 | ftsZ | − | 3599162-3600358 |
| | | acpP | − | 2944967-2945206 |
| | | gyrA | − | 3036533-3039133 |
| Francisella tularensis | NC 006570 | ftsZ | + | 203748-204893 |
| | | acpP | + | 1421900-1422184 |
| | | gyrA | − | 1637300-1639906 |

C. Selection of Oligomer Target Sequences and Lengths

As noted above, the claimed subject matter derives from the discovery herein that oligomeric antisense compounds having at least 10 and up to 20 bases complementary to a bacterial RNA target, e.g., at or just downstream (within 20 bases) of the AUG start site of the mRNA for an essential bacterial protein or a critical rRNA target region, have enhanced anti-bacterial activity as evidence by enhanced inhibition of bacterial growth when they are conjugated to short arginine- and/or lysine-containing peptides. Unconjugated antisense compounds having a ribose or morpholino subunit backbone may be most effective in inhibiting bacterial growth when the subunit length is between 10-12 bases, preferably 11 bases, where the compound contains at least 10 bases, preferably 11-12 bases, that are complementary to the target mRNA sequence. These studies were carried out on bacterial gene expression in pure culture, a bacterial cell-free protein expression system and an in vivo murine peritonitis model, as discussed in detail in the examples below.

Figure 3A:
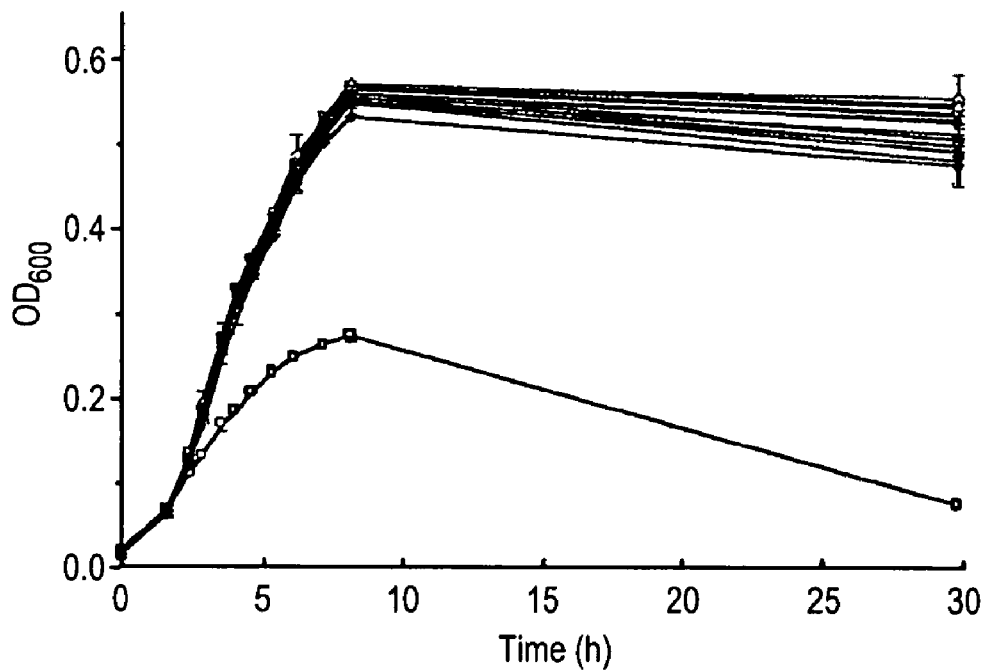
FIGS. 3A and 3B show the effect of AcpP antisense length on growth of *E. coli* AS19. Cultures of *E. coli* AS19 were grown (37° C.) with various lengths (6 to 20 bases) of overlapping PMO (20 μM) targeted to the region around the start codon of the *E. coli* acpP (Table 2, SEQ ID NO:2). Optical density (OD) was monitored over time (FIG. 3A) and open squares indicate culture with 11-base PMO 169 (SEQ ID NO:66) and viable cells (CFU/ml) measured after 8 hours (FIG. 3B).
Figure 3B:
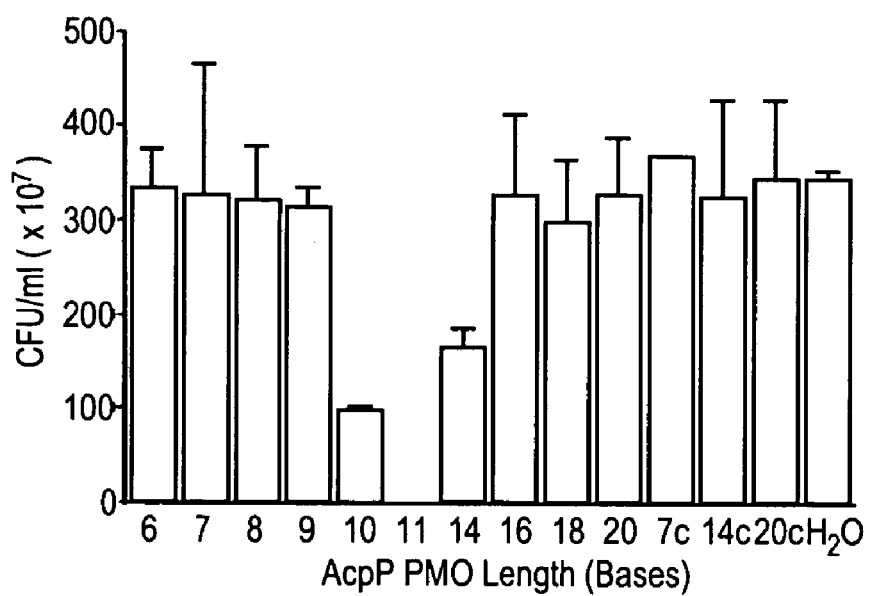
Figure 4:
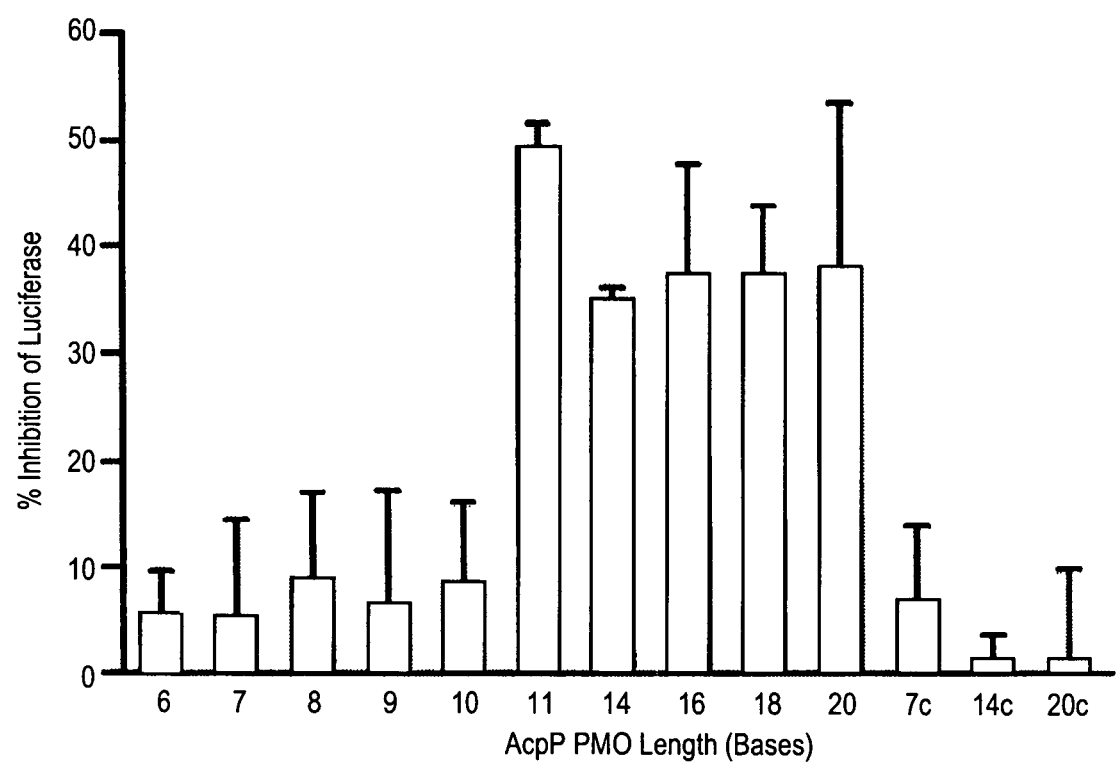
FIG. 4 shows the effect of antisense length on AcpP-luciferase expression in cell-free translation reactions. PMOs of various lengths and targeted around the start codon of acpP (Table 2) were added individually (100 nM) to bacterial cell-free translation reactions programmed to make AcpP-luc.

Antisense compounds directed against the AUG start site region of the bacterial AcpP gene were tested for their ability to inhibit bacterial growth in culture. These studies are reported in Example 1, with reference to FIGS. 3A and 3B. As seen in the latter figure, a striking inhibition was observed for antisense compounds having between 10 and 14 bases, with nearly complete inhibition being observed for the compound with an 11-base length. As with the expression studies involving marker genes described above, the results for inhibition of a bacterial gene in bacteria are unpredictable from the behavior of the same antisense compounds in a cell-free bacterial system. As seen in FIG. 4, strongest inhibition was observed for antisense compounds between 11 and 20 bases.

Figure 12:
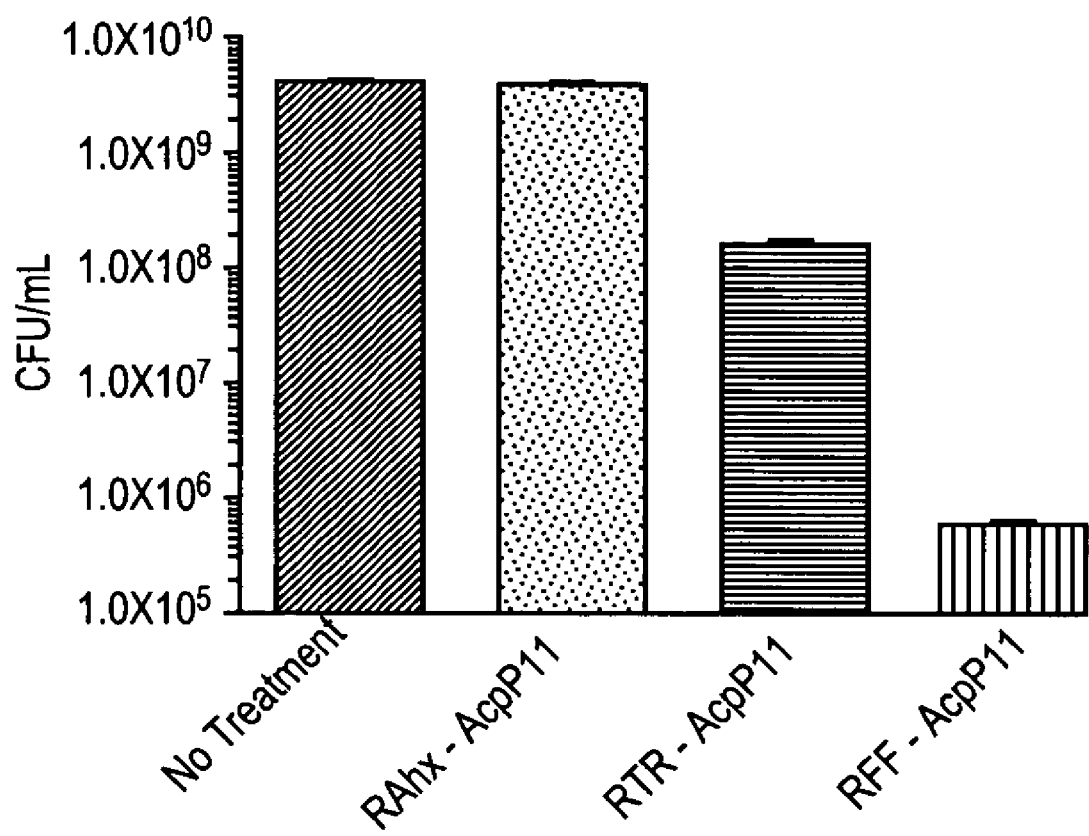
FIG. 12 shows the antibacterial activity of three P-PMOs as measured by CFU/ml after 8 hours of treatment.
Figure 13:
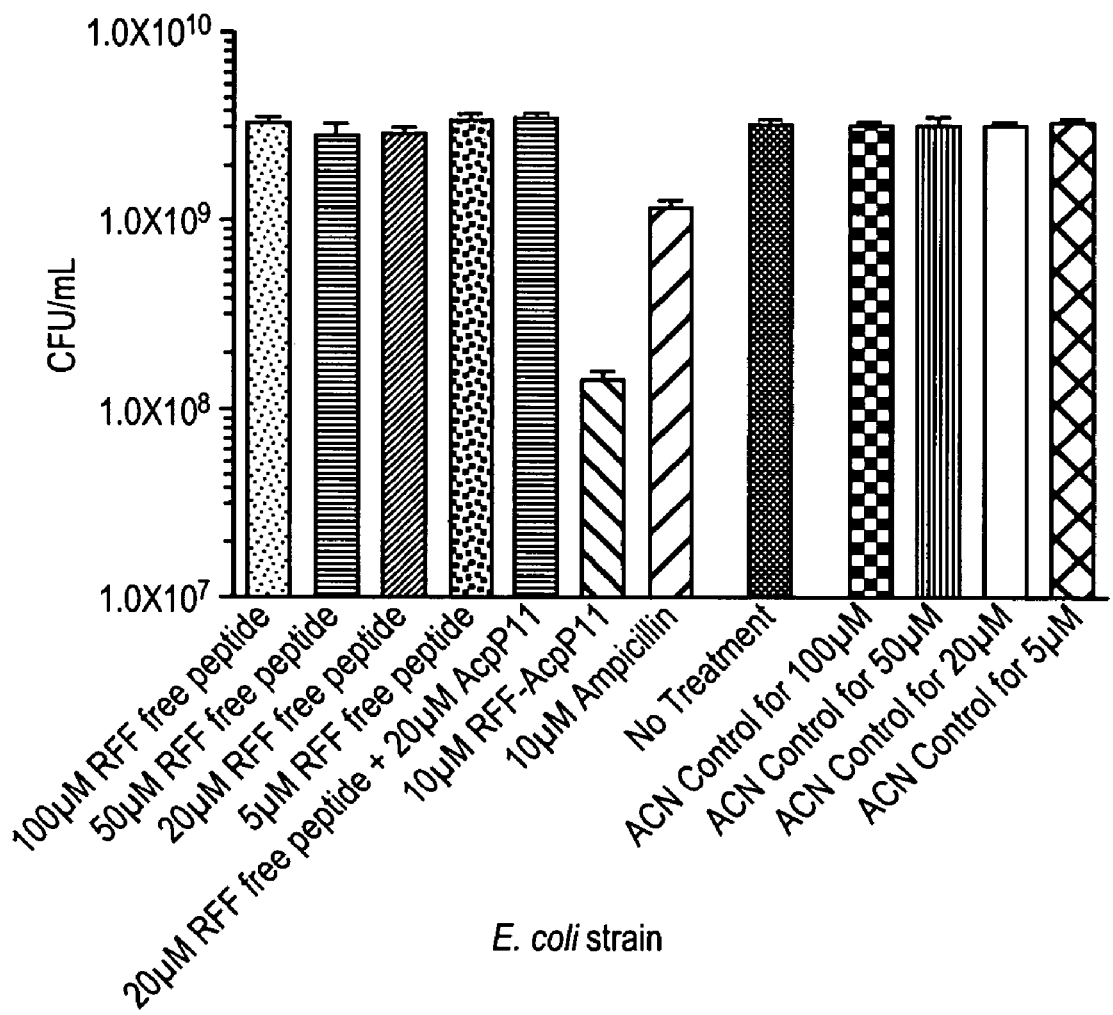
FIG. 13 shows the effect of treatment with a dilution series of RFF peptide, free RFF peptide mixed with AcpP11 PMO, RFF-AcpP11 P-PMO, ampicillin or no treatment.
Figure 14:
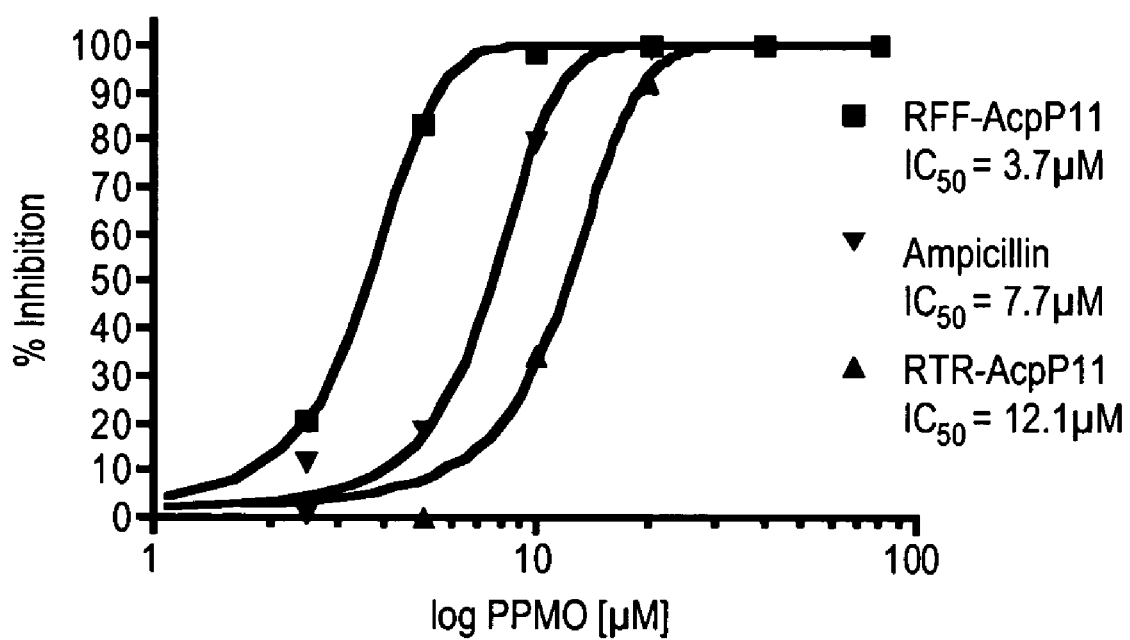
FIG. 14 shows the dose response curves for each of two PPMOs compared to ampicillin and the associated $IC_{50}$ values for RFF-AcpP11, RTR-AcpP11 (SEQ ID NOS:88 and 89) and ampicillin.

As described in Example 3 and shown in FIGS. 7 to 16, conjugation of an arginine-rich peptide to the antisense oligonucleotides described above greatly enhance their antibacterial properties. Exemplary amino acid sequences and the peptides used in experiments in support of the claimed subject matter are listed in Table 4 below as SEQ ID NOS:79-82 and 85-93. One exemplary peptide is named RFF (SEQ ID NO:79) and consists of the sequence N-RFFRFFRFFAhx-βAla-COOH (using the standard one letter amino acid code and Ahx for 6-aminohexanoic acid and βAla for beta-alanine), and has three repeating Arg-Phe-Phe residues. This peptide is representative of one model peptide having at least two, preferably three repeating Arg-Phe-Phe units. One exemplary peptide-conjugated PMO (P-PMO) derived from the RFF peptide (RFF-AcpP11, SEQ ID NO:79) demonstrated the ability to reduce the CFU/ml of E. coli strains by as much as five orders of magnitude (FIG. 11) and an $IC_{50}$ of 3.7 μM that is lower than the 50% inhibitory concentration ($IC_{50}$) observed for ampicillin (7.7 μM) under the same culture conditions (FIG. 14).

More generally, the peptide conjugated to the oligomer in the compound is a peptide of 6-12 residues in length containing at least two, and preferably 2-4 arginine residues, each preferably separated by one or more uncharged, hydrophobic residues. In exemplary embodiments, the carrier peptide has the sequence $(RXX)_n$, where X is an uncharged amino acid selected from the group consisting of alanine, β-alanine, valine, leucine, isoleucine, serine, threonine, phenylalanine, and tryptophan, and n=2 or 3. In preferred embodiments, the carrier peptide has the form $(RFF)_n$ or $(RFF)_nR$, where n=2 or 3. The carrier peptide may be linked at its C-terminus to one end of the oligonucleotide, e.g., the 5'-end, through a one- or two-amino acid linker, such as the linker is AhxβAla, where Ahx is 6-aminohexanoic acid and βAla is β-alanine, and where the linker forms part of the carrier peptide.

The carrier peptides have the ability, when conjugated to the 5' end of the anti-bacterial antisense PMO compound having SEQ ID NO:66, to enhance the anti-bacterial activity of the PMO compound by a factor of at least 10 and typically at least $10^2$, as measured by the reduction in bacterial cell-forming units/ml when the peptide-conjugated PMO compound is added at a concentration of 20 μM in a culture to E coli, strain W3110 for a period of 8 hours, relative to the same activity of the PMO compound alone.

Thus, to determine whether an arginine-rich peptide having a given amino acid sequence is a suitable peptide for the compound of the claimed subject matter, a carrier peptide is synthesized and coupled to the 5' end of the anti-bacterial antisense PMO compound having SEQ ID NO:66, employing synthetic methods described and referenced herein. The conjugate is then added, at a concentration of 20 μM in a culture to E coil, strain W3110 for a period of 8 hours, with the PMO alone (control) being added at a similar concentration to a culture of the same bacteria. After an eight-hour incubation time, the number of colony forming units per ml (CFU/ml) are measured in both the "conjugate" and control cultures. If the CFU/ml count for the conjugate culture is more than 100-fold less, and preferably a 1000-fold less than that of the control culture, the peptide can be identified as one suitable for use in the claimed subject matter.

Based on these considerations, exemplary targeting sequences for use in practicing the claimed invention are those having between 10-20 bases, preferably complete but at least 10-base complementarity with the mRNA target sequence, and complementary to a region of the mRNA that includes the AUG start site or a region up to 20 bases downstream of the start site. Where the compound of the claimed subject matter is used in inhibiting infection by one of the bacteria identified in the table below, by inhibiting one of the three identified bacterial proteins, the antisense oligomer compound has a sequence that is complementary to at least 10 contiguous bases of the corresponding target sequence indicated in the table, where these target sequences are identified in the sequence listing below by SEQ ID NOS:1-61.

TABLE 2

Exemplary bacterial target regions

| Organism (GenBank Ref.) | Target Gene | Nucleotide Region | SEQ ID NO. |
|---|---|---|---|
| Escherichia coli | ftsZ | 105295-105325 | 1 |
| (NC 000913) | acpP | 1150828-1150858 | 2 |
|  | gyrA | 2337422-2337452 | 3 |
| Escherichia coli 0157:H7 | ftsZ | 109901-109931 | 4 |
| (NC 002655) | acpP | 1595786-1595816 | 5 |
|  | gyrA | 3136439-3136469 | 6 |
| Salmonella thyphimurium | ftsZ | 155673-155703 | 7 |
| (NC 003197) | acpP | 1280103-1280133 | 8 |
|  | gyrA | 2376327-2376357 | 9 |
| Pseudomonas aeruginosa | ftsZ | 4940463-4940493 | 10 |
| (NC 002516) | acpP | 3325162-3325192 | 11 |
|  | gyrA | 3559177-3559207 | 12 |
| Vibrio cholera | ftsZ | 2566223-2566253 | 13 |
| (NC 002505) | acpP | 254495-254525 | 14 |
|  | gyrA | 1330197-1330227 | 15 |
| Neisseria gonorrhoea | ftsZ | 1500031-1500060 | 16 |
| (NC 002946) | acpP | 1724391-1724420 | 17 |
|  | gyrA | 621170-621199 | 18 |
| Staphylococcus aureus | ftsZ | 1165772-1165802 | 19 |
| (NC 002745) | gyrA | 6995-7025 | 20 |
|  | fmhB | 2322402-2322431 | 21 |
| Mycobacterium tuberculosis | ftsZ | 2408265-2408295 | 22 |
| (NC 002755) | acpP | 1510172-1510202 | 23 |
|  | gyrA | 7292-7322 | 24 |
|  | pimA | 2935126-2935126 | 25 |
|  | cysS2 | 4015924-4015953 | 26 |
| Helicobacter pylori | ftsZ | 1042227-1042257 | 27 |
| (NC 000915) | acpP | 594253-594283 | 28 |
|  | gyrA | 752502-752532 | 29 |
| Streptococcus pneumoniae | ftsZ | 1566686-1566716 | 30 |
| (NC 003028) | acpP | 396681-396711 | 31 |
|  | gyrA | 1149835-1149865 | 32 |
| Treponema palladium | ftsZ | 414741-414771 | 33 |
| (NC 000919) | acpP | 877626-877656 | 34 |
|  | gyrA | 4381-4411 | 35 |
| Chlamydia trachomatis | acpP | 263915-263945 | 36 |
| (NC 000117) | gyrA | 756474-756504 | 37 |
| Bartonella henselae | ftsZ | 1232075-1232104 | 38 |
| (NC 005956) | acpP | 623133-623162 | 39 |
|  | gyrA | 1123338-1123367 | 40 |
| Hemophilis influenza | ftsZ | 1212011-1212041 | 41 |
| (NC 000907) | acpP | 171140-171170 | 42 |
|  | gyrA | 1344341-1344371 | 43 |
| Listeria monocytogenes | ftsZ | 2102288-2102307 | 44 |
| (NC 002973) | acpP | 1860519-1860548 | 45 |
|  | gyrA | 8055-8084 | 46 |
| Yersinia pestis | ftsZ | 605864-605893 | 47 |
| (NC 003143) | acpP | 1824110-1824139 | 48 |
|  | gyrA | 1370719-1370748 | 49 |
| Bacillus anthracis | ftsZ | 3725338-3725367 | 50 |
| (NC 005945) | acpP | 3666877-3666906 | 51 |
|  | gyrA | 6586-6615 | 52 |
| Burkholderia mallei | ftsZ | 2650793-2650822 | 53 |
| (NC 006348) | acpP | 559420-559449 | 54 |
|  | gyrA | 461883-461912 | 55 |
| Burkholderia pseudomallei | ftsZ | 3600339-3600368 | 56 |
| (NC 006350) | acpP | 2945187-2945216 | 57 |
|  | gyrA | 3039114-3039143 | 58 |
| Francisella tularensis | ftsZ | 203738-203767 | 59 |
| (NC 006570) | acpP | 1421890-1421919 | 60 |
|  | gyrA | 1639887-1639916 | 61 |

Any essential bacterial gene can be targeted using the methods of the claimed subject matter. As described above, an essential bacterial gene for any bacterial species can be determined using a variety of methods including those described by Gerdes for *E. coli* (Gerdes, Scholle et al. 2003). Many essential genes are conserved across the bacterial kingdom thereby providing additional guidance in target selection. Target regions can be obtained using readily available bioinformatics resources such as those maintained by the National Center for Biotechnology Information (NCBI). Complete reference genomic sequences for a large number of microbial species can be obtained (e.g., see http://www.ncbi.nlm.nih-.gov/genomes/lproks.cgi) and sequences for essential bacterial genes identified. Bacterial strains can be obtained from the American Type Culture Collection (ATCC). Simple cell culture methods, such as those described in the Examples, using the appropriate culture medium and conditions for any given species, can be established to determine the antibacterial activity of antisense compounds. Once a suitable targeting antisense oligomer has been identified, the peptide moieties of the compounds can be altered to obtain optimal antibacterial activity. An optimal peptide moiety can then be fixed and alternative antisense moieties tested for improved antibacterial activity. One or more iterations of this process can lead to compounds with improved activity but, in general, no more than two iterations are needed to identify highly active antibacterial agents.

The first step in selecting a suitable antisense compound is to identify, by the methods above, a targeting sequence that includes the AUG start site and/or contains at least about 10-20 bases downstream of the start site. Table 2 above gives the base-number locations of 30- to 31-base targeting sequences that span the AUG start site by about 10 bases on the upstream (5' side) and about 20 bases (including the start site) in the downstream coding region. The actual target sequences corresponding to these target-site locations are given in the sequence listing below, identified by SEQ ID NOS:1-61.

For purposes of illustration, assume that the antisense compound to be prepared is for use in inhibiting an *E. coli* bacterial infection in an individual infected with *E. coli* strain 0157:H7, and that the essential gene being targeted is the *E. coli* acpP gene. One suitable target sequence for this gene identified by the methods above is SEQ ID NO:2 having the sequence 5'-ATTTAAGAGTATGAGCACTATCGGMGM-CGC-3' where the sequence gives the DNA thymine (T) bases rather than the RNA uracil (U) bases, and where the AUG start site (ATG) is shown in bold.

Again, for purposes of illustration, four model antisense targeting sequences, each of them 11 bases in length, are selected: (i) an antisense sequence that spans the AUG start site with four bases of each side and has the sequence identified by SEQ ID NO:94; (ii) an antisense sequence that overlaps the AUG starts at its 5' end and extends in a 3' direction an additional 8 bases into the coding region of the gene, identified as SEQ ID NO:95; (iii) an antisense sequence complementary to bases 5-15 of the gene's coding region, identified as SEQ ID NO:66, and (iv) an antisense sequence complementary to bases 11-21 of the gene's coding region, identified as SEQ ID NO:96.

Once antisense sequences have been selected and the antisense compound synthesized and conjugated to arginine and/or lysine-containing peptides, the compounds may be tested for the ability to inhibit bacterial growth, in this case growth of an *E. coli* strain in culture. Following the protocol in Example 1, for example, the four 11 mer sequences described above are individually tested for optimal activity, e.g., maximum drop in CFU/ml at a given dose, e.g., 5-20 µM, against an *E. coli* culture. Compound(s) showing optimal activity are then tested in animal models, as described in Example 2, or veterinary animals, prior to use for treating human infection.

IV. Method for Inhibiting Bacteria

In one aspect, the claimed subject matter includes a method of inhibiting bacterial infection, by exposing the infecting bacteria to a 10-20 base peptide-conjugated oligomeric antisense compound of the type characterized above. This general method is demonstrated by the study reported in Example 1 and described above with respect to FIGS. 3A and 3B.

Figure 5:
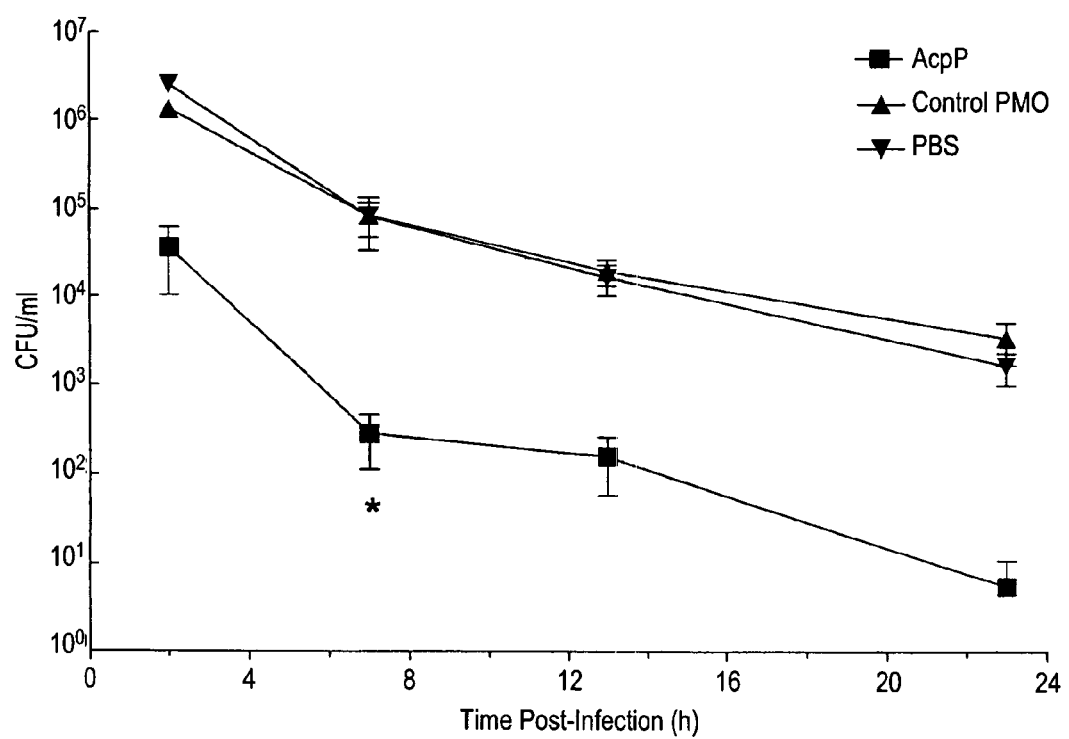
FIG. 5 shows CFU/ml in peritoneal lavages from mice infected with permeable *E. coli* strain AS19 and treated with acpP PMO (■; SEQ ID NO:66), nonsense PMO (▲), or PBS (▼) at 0 hours. At each time indicated, peritoneal lavage was collected and analyzed for bacteria (CFU/ml) from 3 mice in each treatment group.

In one aspect, the method is applied to inhibiting a bacterial infection in a mammalian subject, including a human subject, by administering the antisense compound to the subject in a therapeutic amount. To demonstrate the method, groups of 12 mice were injected IP with *E. coli* AS19, which has a genetic defect that makes it abnormally permeable to high MW solutes. Immediately following infection, each mouse was injected IP with 300 μg of an 11-base PMO complementary to acpP (SEQ ID NO:66), an 11-base nonsense sequence PMO, or PBS, as detailed in Example 2. As seen in FIG. 5, mice treated with the target antisense showed a reduction in bacterial CFUs of about 600 at 23 hours, compared with control treatment.

Figure 6:
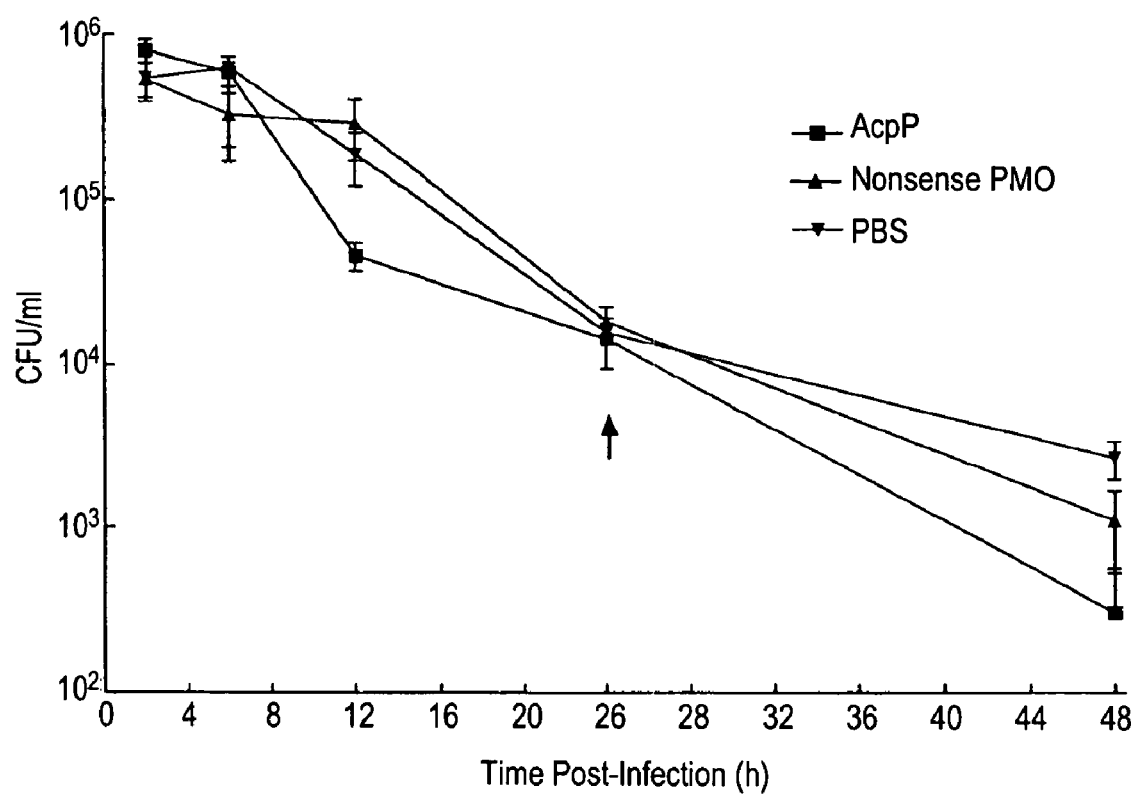
FIG. 6 shows CFU/ml in peritoneal lavages from mice infected *E. coli* strain SM105 and treated with PMO as described in FIG. 13.
Figure 7:
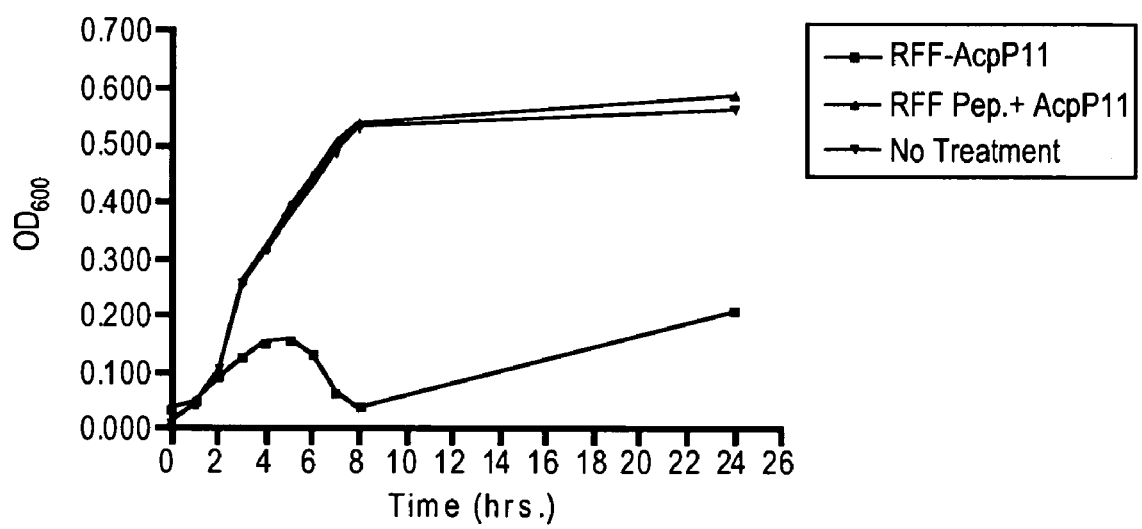
FIGS. 7 to 10 show the growth as measured by optical density ($OD_{600}$) of four strains of *E. coli* grown for 24 hours in the presence of the peptide-conjugated PMO (P-PMO) RFF-AcpP11 (SEQ ID NO:79) compared to no treatment and treatment with a mixture of the AcpP11 PMO and the RFF peptide (SEQ ID NOS:66 and 79, respectively).
Figure 8:
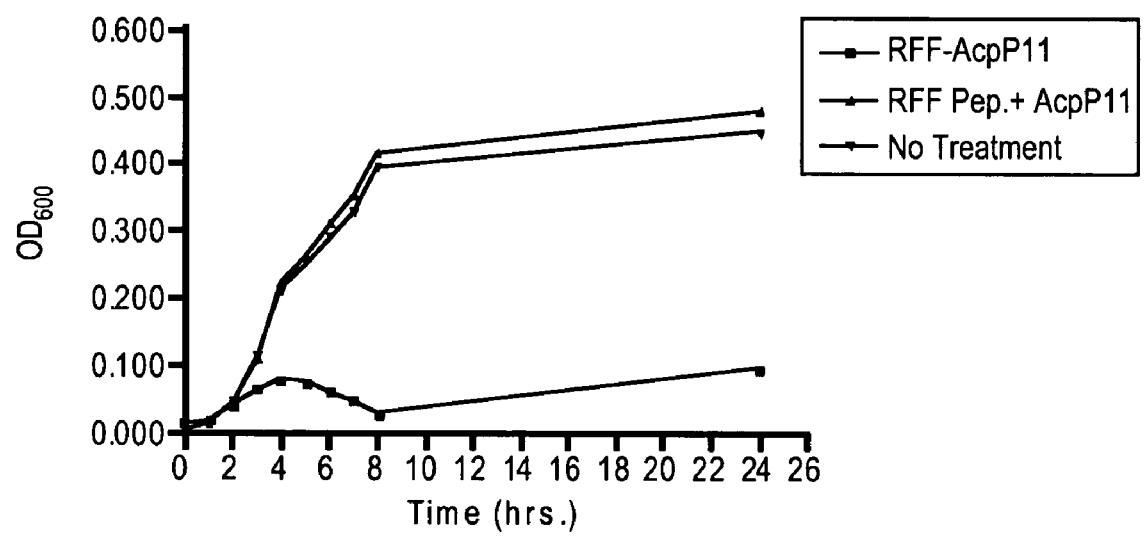
Figure 9:
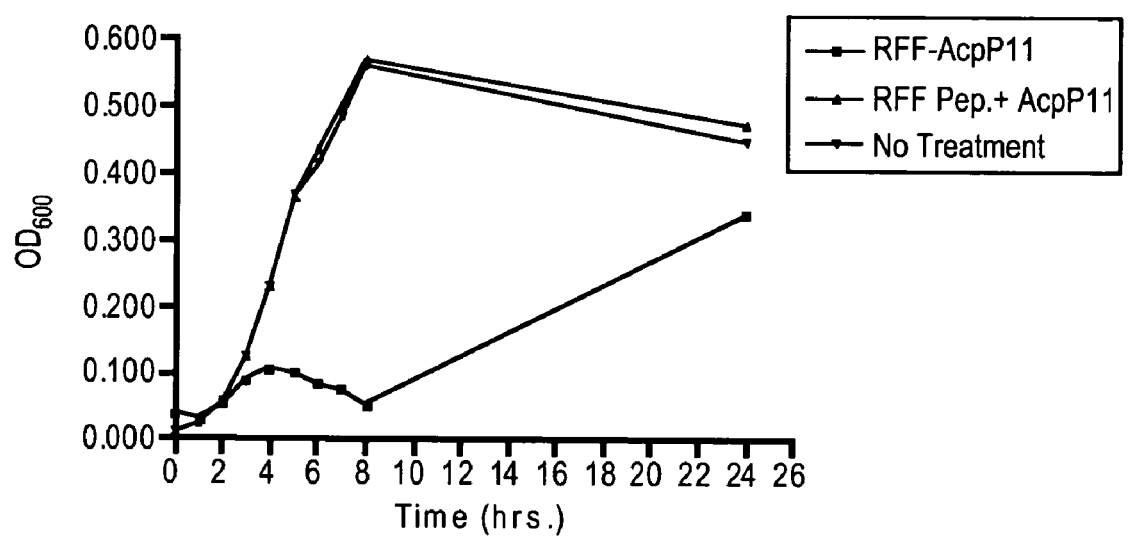
Figure 10:
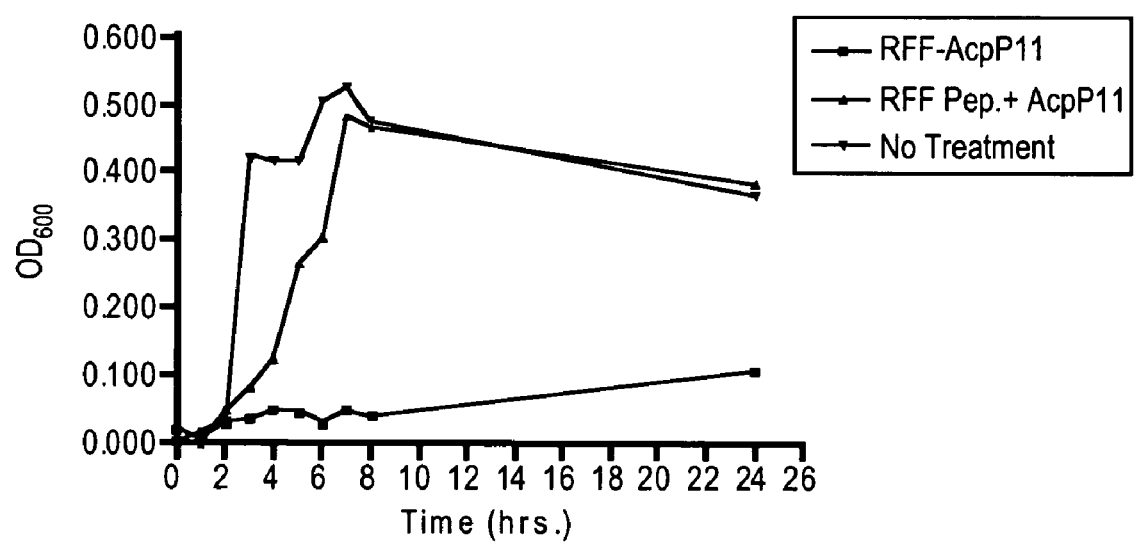

The same PMOs were again tested, except with *E. coli* SM105, which has a normal outer membrane. In this method, acpP PMO reduced CFU by 84% compared to nonsense PMO at 12 hours post-infection. There was no reduction of CFU at 2, 6, or 24 hours (FIG. 6). Mice were injected with a second dose at 24 hours post-infection. By 48 hours post-infection the CFU of acpP PMO-treated mice were 70% lower than the CFU of nonsense PMO-treated mice (FIG. 6).

To demonstrate that the effect on bacterial infection was sequence specific, a luciferase reporter gene whose expression would not affect growth was used, and luciferase expression was measured directly by two independent criteria, luciferase activity and luciferase protein abundance. As detailed in Example 2, the study demonstrated that an antisense compound complementary to the luciferase mRNA inhibited luciferase expression at two different times after administration of the PMO. Moreover, inhibition was quantitatively similar with both methods of measurement. These results show directly that PMO inhibit bacterial target gene expression in vivo in a sequence-specific manner.

An improved antibacterial PMO can be obtained by conjugating a short 6-12 amino acid peptide that enhances either intracellular delivery or antisense activity or both. Exemplary peptides and peptide-conjugated PMO (P-PMO) are listed in Table 4 as SEQ ID NOS:88-93. As described in Example 3, enhanced antibacterial activity was observed in pure culture experiments using a variety of *E. coli* and *S. typhimurium* strains including the clinically isolated enterpathogenic *E. coli* (EPEC) strain O127:H6. Example 4 describes the antibacterial activity of peptide-conjugated PMO targeted to *B. cenocepacia* and *P. aeruginosa*.

It will be understood that the in vivo efficacy of such a peptide-conjugated antisense oligomer in a subject using the methods of the claimed invention is dependent upon numerous factors including, but not limited to, (1) the target sequence; (2) the duration, dose and frequency of antisense administration; and (3) the general condition of the subject.

In other cases, the antisense oligonucleotides of the claimed subject matter find utility in the preparation of antibacterial vaccines. In this aspect of the claimed subject matter, a culture of a particular type of bacteria is incubated in the presence of a morpholino-based, peptide-conjugated antisense oligomer of the type described above, in an amount effective to produce replication-crippled and/or morphologically abnormal bacterial cells. Such replication-crippled and/or morphologically abnormal bacterial cells are administered to a subject and act as a vaccine.

The efficacy of an in vivo administered antisense oligomer of the claimed subject matter in inhibiting or eliminating the growth of one or more types of bacteria may be determined by in vitro culture or microscopic examination of a biological sample (tissue, blood, etc.) taken from a subject prior to, during and subsequent to administration of the peptide-conjugated antisense oligomer. (See, for example, (Pari, Field et al. 1995); and (Anderson, Fox et al. 1996). The efficacy of an in vivo administered vaccine of peptide-conjugated, antisense oligomer-treated bacteria may be determined by standard immunological techniques for detection of an immune response, e.g., ELISA, Western blot, radioimmunoassay (RIA), mixed lymphoctye reaction (MLR), assay for bacteria-specific cytotoxic T lymphocytes (CTL), etc.

A. Administration Methods

Effective delivery of the peptide-conjugated antisense oligomer to the target nucleic acid is an important aspect of treatment. In accordance with the claimed invention, such routes of delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of a peptide-conjugated antisense oligomer in the treatment of a bacterial infection of the skin is topical delivery; while delivery of a peptide conjugated antisense oligomer in the treatment of a bacterial respiratory infection is by inhalation. Methods effective to deliver the oligomer to the site of bacterial infection or to introduce the compound into the bloodstream are also contemplated.

Transdermal delivery of peptide-conjugated antisense oligomers may be accomplished by use of a pharmaceutically acceptable carrier adapted for e.g., topical administration. One example of morpholino oligomer delivery is described in PCT patent application WO 97/40854, incorporated herein by reference.

In one preferred embodiment, the compound is a peptide-conjugated morpholino oligomer, contained in a pharmaceutically acceptable carrier, and is delivered orally.

The peptide-conjugated antisense oligonucleotide may be administered in any convenient vehicle which is physiologically acceptable. Such a composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of the antisense oligonucleotide into cells. (See, e.g., Williams, S. A., *Leukemia* 10 (12):1980-1989, 1996; Lappalainen et al., *Antiviral Res.* 23:119, 1994; Uhlmann et al., ANTISENSE OLIGONUCLEOTIDES: A NEW THERAPEUTIC PRINCIPLES, *Chemical Reviews*, Volume 90, No. 4, pages 544-584, 1990; Gregoriadis, G., Chapter 14, Liposomes, *Drug Carriers in Biology and Medicine*, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., *J. Biol. Chem.* 262:4429-4432, 1987.)

Sustained release compositions are also contemplated within the scope of this application. These may include semi-permeable polymeric matrices in the form of shaped articles such as films or microcapsules.

Typically, one or more doses of peptide-conjugated antisense oligomer are administered, generally at regular intervals for a period of about one to two weeks. Preferred doses for oral administration are from about 10 mg oligomer/patient to about 250 mg oligomer/patient (based on a weight of 70 kg). In some cases, doses of greater than 250 mg oligomer/patient may be necessary. For IV administration, the preferred doses are from about 1.0 mg oligomer/patient to about 100 mg oligomer/patient (based on an adult weight of 70 kg). The peptide-conjugated antisense compound is generally administered in an amount and manner effective to result in a peak blood concentration of at least 200-400 nM oligomer.

In a further aspect of this embodiment, a peptide-conjugated morpholino antisense oligonucleotide is administered at regular intervals for a short time period, e.g., daily for two weeks or less. However, in some cases the peptide-conjugated antisense oligomer is administered intermittently over a longer period of time. Administration of a peptide-conjugated morpholino antisense oligomer to a subject may also be followed by, or concurrent with, administration of an antibiotic or other therapeutic treatment.

In one aspect of the method, the subject is a human subject, e.g., a patient diagnosed as having a localized or systemic bacterial infection. The condition of a patient may also dictate prophylactic administration of a peptide-conjugated antisense oligomer of the claimed subject matter or a peptide-conjugated antisense oligomer treated bacterial vaccine, e.g. in the case of a patient who (1) is immunocompromised; (2) is a burn victim; (3) has an indwelling catheter; or (4) is about to undergo or has recently undergone surgery.

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antibacterial antisense compound of the type described above. Also contemplated is in a method of feeding livestock and poultry with a food grain supplemented with subtherapeutic levels of an antibiotic, an improvement in which the food grain is supplemented with a subtherapeutic amount of an antibacterial oligonucleotide composition as described above.

The methods of the invention are applicable, in general, to treatment of any condition wherein inhibiting or eliminating the growth of bacteria would be effective to result in an improved therapeutic outcome for the subject under treatment.

One aspect of the invention is a method for treatment of a bacterial infection which includes the administration of a morpholino antisense oligomer to a subject, followed by or concurrent with administration of an antibiotic or other therapeutic treatment to the subject.

B. Treatment Monitoring Methods

It will be understood that an effective in vivo treatment regimen using the peptide-conjugated antisense oligonucleotide compounds of the invention will vary according to the frequency and route of administration, as well as the condition of the subject under treatment (i.e., prophylactic administration versus administration in response to localized or systemic infection). Accordingly, such in vivo therapy will generally require monitoring by tests appropriate to the particular type of bacterial infection under treatment and a corresponding adjustment in the dose or treatment regimen in order to achieve an optimal therapeutic outcome.

The efficacy of a given therapeutic regimen involving the methods described herein may be monitored, e.g., by general indicators of infection, such as complete blood count (CBC), nucleic acid detection methods, immunodiagnostic tests, or bacterial culture.

Identification and monitoring of bacterial infection generally involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses (i.e., oxidase, catalase positive for *Pseudomonas aeruginosa*), and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The peptide-conjugated antisense oligomer treatment regimen may be adjusted (dose, frequency, route, etc.), as indicated, based on the results of immunoassays, other biochemical tests and physiological examination of the subject under treatment.

From the foregoing, it will be appreciated how various objects and features of the invention are met. The method provides an improvement in therapy against bacterial infection, using peptide-conjugated antisense oligonucleotide sequences to achieve enhanced cell uptake and anti-bacterial action. As a result, drug therapy is more effective and less expensive, both in terms of cost and amount of compound required.

An important advantage of the invention is that compounds effective against virtually any pathogenic bacterium can be readily designed and tested, e.g., for rapid response against new drug-resistant bacteria, or in cases of bioterrorism. Once a target bacterium is identified, the sequence selection methods described allow one to readily identify one or more likely gene targets, among a number of essential genes, and prepare antisense compounds directed against the identified target. Because clinical testing on the safety and efficacy, once established for a small group of compounds, can be extrapolated to virtually any new target, relatively little time is needed in addressing new bacterial-infection challenges as they arise.

The following examples are intended to illustrate but not to limit the invention.

Materials and Methods

Phosphorodiamidate Morpholino Oligomers

PMO were synthesized and purified at AVI BioPharma, Inc. (Corvallis, Oreg.) as previously described (Summerton and Weller 1997; Geller, Deere et al. 2003), dissolved in water, filtered through a 0.2 μM membrane (HT Tuffryn®, Gelman Sciences, Inc., Ann Arbor, Mich.), and stored at 4° C. Sequences of PMO used in this study are shown in Table 3. The concentration of PMO was determined spectrophotometrically by measuring the absorbance at 260 nm and calculating the molarity using the appropriate extinction coefficient.

Peptide Synthesis and Conjugation to PMO

Peptide synthesis of RFF (CP04073, (RFF)$_3$AhxβAla), SEQ ID NO:79 and RTR (CP04074, RTRTRFLRRTAhx-βAla, SEQ ID NO:80) and conjugation to PMO were performed using the following techniques. All the peptides of the present invention can be synthesized and conjugated to PMO using these synthetic techniques.

Peptides were synthesized by Fmoc Solid Phase Peptide Synthesis, referred to herein as SPPS. A p-benzyloxybenzyl alcohol resin was used for synthesis of peptides (Novabiochem, San Diego, Calif.). A typical synthesis cycle began with N-terminal deprotection via 20% piperidine. Then, N-α-Fmoc-protected amino acids were coupled to the growing peptide chain by activation with 2-(1H-Benzotriazole-1-yl)-1,1,3,3-tetramethyluronium hexafluorophosphate (HBTU) in the presence of N,N-diisopropylethylamine (DIEA). Arginine side chains were protected with the 2,2,4,6,7-pentamethyldihydrobenzofuran-5-sulfonyl (Pbf) protecting group and the t-Butyl (tBu) group for tyrosine side chains. The cycle was repeated until all of the amino acids were added, in a carboxy-to-amino direction, in the desired sequence. Cleavage from the synthesis resin and side chain deprotection of the CP04073 peptide were carried out simultaneously by treating the peptidyl-resin with a solution of 5% H$_2$O and 95% trifluoroacetic acid (TFA). For the CP04074 peptide residue, a cleavage cocktail of 81.5% TFA, 5% Thioanisole, 5% Phenol, 5% H$_2$O, 2.5% 1,2-ethanedithiol (EDT) and 1% triisopropyl silane (TIS) was used for simultaneous cleavage and side chain deprotection. Crude peptides were isolated by precipitation using a tenfold excess of diethyl ether. Strong cation exchange HPLC utilizing Source 15S resin (Amersham Biosciences, Piscataway, N.J.) was used for purification, followed by a reversed phase desalt employing Amberchrom 300M resin (Tosoh Bioscience, Montgomeryville, Pa.). Desalted peptides were lyophilized and analyzed for identity and purity by matrix assisted laser desorption ionization time of flight mass spectroscopy (MALDI-TOF MS) and strong cation exchange high performance liquid chromatograph (SCX HPLC).

Attachment of the peptides at the 5' termini of the PMO was performed via an amide bond as follows. A C-terminally reactive peptide-benzotriazolyl ester was prepared by dissolving the peptide-acid (15 μmol), HBTU (14.25 μmol), and HOBt (15 μmol) in 200 μL NMP and adding DIEA (22.5 μmol). Immediately after addition of DIEA, the peptide solution was added to 1 mL of a 12 mM solution of 5'-piperazine-functionalized, 3'-acetyl-PMO in DMSO. After 180 minutes at 30° C., the reaction was diluted with a four-fold excess of water. The crude CP04074 conjugate was purified first through a CM-Sepharose weak cation exchange column (Sigma, St. Louis, Mo.) to remove unconjugated PMO, and then through a reversed phase column (Amberchrom 300M resin (Tosoh Bioscience, Montgomeryville, Pa.). The crude CP04073 conjugate was purified by resolving chromatography using strong cation exchange resin (Source 30S, Amersham Biosciences, Piscataway, N.J.) to remove unconjugated PMO and excess peptide. The SCX chromatography was followed by a reverse phase column (Amberchrom 300M resin (Tosoh Bioscience, Montgomeryville, Pa.). The conjugates were lyophilized and analyzed by MALDI-TOF MS and SCX HPLC.

Bacteria and Growth Conditions

Bacterial strains were obtained from the American Type Culture Collection (ATCC) or the E. coli Genetic Stock Center at Yale University. E. coli strain AS19 was obtained from Dr. Pete Nielsen (University of Copenhagen, Denmark). All pure culture experiments were done in 96-well plates. OD600 readings and plating of cells for CFU/ml determinations were done in triplicate. E. coli AS19 and SM101, which have defects in lipopolysaccharide synthesis that result in outer membrane permeability to high MW solutes, were grown aerobically in LB broth at 37° C., and 30° C., respectively.

E. coli AS19 and SM105 were grown in LB broth (supplemented with 100 μg/ml ampicillin for transformants that expressed luciferase) to OD$_{600}$=0.12, centrifuged (4,000×g, 10 min, 20° C.), and resuspended in 5% mucin (type II, Sigma Chemical Co., St. Louis,)/PBS to final concentrations as follows: AS19, 1.5×10$^8$ CFU/ml; SM105, 5.7×10$^7$ CFU/ml; AS19 (pT7myc-luc), 7.2×10$^9$ CFU/ml.

Reporter Gene

Standard molecular biology procedures were used for all constructions. All constructs were sequenced. The acpP-luc reporter (pCNacpP-luc) was made by ligating a SalI-NotI restriction fragment of luc with the SalI-NotI fragment of pCiNeo (Promega Corp., Madison, Wis.), removing the adenosine from the start codon by site-directed mutagenesis, then directionally cloning a synthetic fragment of E. coli acpP (bp −17 to +23, inclusive, where +1 is adenosine of the start codon) between the NheI-SalI sites. Luciferase enzyme activity was measured in bacteria as described (Geller, Deere et al. 2003).

Cell-free Protein Synthesis

Bacterial, cell-free protein synthesis reactions were performed by mixing reactants on ice according to the manufacturer's instruction (Promega Corp.). Reactions were programmed with mRNA synthesized in a cell-free RNA synthesis reaction (Ambion, Inc., Austin, Tex., MEGAscript T7 High Yield Transcription Kit) programmed with pCNacpP-luc. Where indicated, cell-free reactions were composed with rabbit reticulocyte lysate as described by the manufacturer (Promega Corp.). PMO was added to a final concentration of either 100 nM or 200 nM as indicated. After 1 hour at 37° C., the reactions were cooled on ice and luciferase was measured as described (Geller, Deere et al. 2003).

Mammalian Tissue Culture

HeLa cells were transfected in T75 tissue culture flasks (Nalge Nunc, Inc., Rochester, N.Y.) with a luciferase reporter plasmid (pCNmyc-luc) using Lipofectamine Reagent (Gibco BRL, Grand Island, N.Y.,) according to user's manual in serum-free media (Gibco, Inc., Carlsbad, Calif., Opti-MEM1) for 5 hours before re-addition of growth medium (Hyclone, Inc., Logan, Utah, HyQ DME/F12 supplemented with 10% Fetal Bovine Serum and Gibco Antibiotic-Antimycotic 15240-062) at 37° C. in 5% CO$_2$. After 24 hours, the cells were pooled and 1×10$^6$ were added to each well of a 6-well plate (BD Biosciences, San Jose, Calif.) in 2 ml of growth media. After an additional 24 hours, PMO was added to a final concentration of 10 μM in 2 ml fresh growth media and the cells were scraped from the plate surface with a rubber policeman to deliver the PMO to the cell as previously described (Partridge, Vincent et al. 1996). After scrape-loading, the cells were transferred to fresh 6-well plates and incubated at 37° C. until the time of assay. At 7 and 24 hours the cells were examined by microscopy to verify that each culture had the same number of cells, harvested by centrifugation, and lysed in Promega Cell Culture Lysis Reagent (Promega Corp.). Luciferase was measured by mixing the cell lysate with Luciferase Assay Reagent (Promega Corp.) and reading light emission in a Model TD-20e luminometer (Turner Designs, Inc., Mountain View, Calif.).

Animals

Female, 6 to 8 week old Swiss Webster mice (Simonsen Labs, Inc., Gilroy, Calif.) were used in all but one experiment, but identical results were obtained with males. Infection was established as described in (Frimodt-Moller, Knudsen et al. 1999). Each mouse was injected IP with 0.1 ml of bacteria resuspended in 5% mucin/PBS, then immediately injected IP with 0.1 ml of PMO (3.0 mg/ml) or PBS. At various times after infection (as indicated in the figures), groups (n=3 to 5) of mice were injected IP with 2.0 ml PBS, and their abdomens gently massaged for 2 min. Peritoneal lavage was removed and stored on ice for ~1 hour. The lavages were diluted in PBS and plated in triplicate on LB to determine CFU.

Luciferase and Western Blot

Peritoneal lavages (1.00 ml) from mice infected with AS19 (pT7myc-luc) were centrifuged (10,000×g, 2 min, 4° C.) and the supernatants discarded. The pellets were resuspended in 50 µl PBS. An aliquot of resuspended cells was mixed with an equal volume of 2× cell culture lysis reagent (Promega, Inc., Madison, Wis.) and frozen at −85° C. Frozen lysates were thawed and luciferase light production was measured in duplicate in a luminometer as described (Geller, Deere et al. 2003). A second aliquot of the cell suspension was mixed with 2× SDS sample buffer and analyzed by western blot using 4-20% gradient Gene Mate Express Gels (ISC BioExpress, Inc., Kaysville, Utah.). Blots were prepared with primary antibody to luciferase (Cortex Biochmical, San Leandro, Calif.) or antisera to OmpA (Geller and Green 1989), secondary goat anti-rabbit IgG-horse radish peroxidase conjugate (Santa Cruz Biotechnology, Inc., Santa, Cruz, Calif.), and ECL Western Blotting Reagent (Amersham Biosciences, Buckinghamshire, England). Film negatives were scanned and digitized on an Kodak Image Station 440 CF. The net intensity of each band was calculated by subtracting the mean background intensity. Luciferase protein was normalized to OmpA by dividing the net intensity of the luciferase band by the net intensity of the OmpA band in the same sample. The % inhibition was calculated by subtracting the mean luciferase/OmpA of luc PMO-treated mice from mean luciferase/OmpA of nonsense PMO-treated mice, dividing the difference by mean luciferase/OmpA of nonsense PMO-treated mice, then multiplying by 100%.

Statistical Analysis

Spearman's rank-order correlation was used to analyze correlations between the inhibitory effects of PMO and either G+C content or secondary structure score of each PMO. Individual mouse CFU/ml values were transformed logarithmically for statistical analysis using InStat statistical software (GraphPad Software, San Diego, Calif.). Differences in treatment group means were analysed with upaired t test, not assuming equal variances, with Welch correction. Treatment group values were analysed for Gaussian distributions using the method of Kolmogorov and Smirnov, which confirmed in all analyses the normality test of the data. A one-tailed t test was applied to differences in means between AcpP PMO and either PBS or scrambled PMO treatment groups, whereas two-sided t test was applied in all other analyses.

Oligomer Sequences

Exemplary targeting oligomers used in describing the present invention are listed below in Table 3. The listed oligomers all target *E. coli*, the experimental bacterial strain used in experiments in support of the invention. Table 4 lists the peptides of the invention and the peptide-PMO conjugates used in experiments in support of the invention.

TABLE 3

PMO Sequences

| PMO # | Sequence (5' to 3') | Target | SEQ ID NO |
|---|---|---|---|
| 62-1 | TTC TTC GAT AGT GCT CAT AC | acpP - 20mer | 62 |
| 62-2 | TC TTC GAT AGT GCT CAT A | acpP - 18mer | 63 |
| 62-3 | C TTC GAT AGT GCT CAT | acpP - 16mer | 64 |
| 62-4 | TC GAT AGT GCT CAT | acpP - 14mer | 65 |
| 169 | C TTC GAT AGT G | acpP - 11mer | 66 |
| 379 | TTC GAT AGT G | acpP - 10mer | 67 |
| 380 | TTC GAT AGT | acpP - 9mer | 68 |
| 381 | TC GAT AGT | acpP - 8mer | 69 |
| 382 | TC GAT AG | acpP - 7mer | 70 |
| 383 | C GAT AG | acpP - 6mer | 71 |
| 62-5 | TTG TCC TGA ATA TCA CTT CG | Nonsense control-acpP | 72 |
| 62-7 | G TCC TGA ATA TCA CTT | Nonsense control-acpP | 73 |
| 62-8 | TCG TGA GTA TCA CT | Nonsense control-acpP | 74 |
| 170 | TCT CAG ATG GT | Nonsense control-acpP | 75 |
| 384 | AAT CGG A | Nonsense control-acpP | 76 |
|  | ACG TTG AGG C | luc | 77 |
|  | TCC ACT TGC C | luc nonsense | 78 |

TABLE 4

Peptide and Peptide-PMO Sequences

| Name | Sequence (Amino to Carboxy Terminus, 5' to 3') | SEQ ID NO |
|---|---|---|
| RFF | N-RFFRFFRFFAhxβAla-COOH | 79 |
| RTR | N-RTRTRFLRRTAhxβAla-COOH | 80 |
| RFFR | N-RFFRFFRFFRAhxβAla-COOH | 81 |
| KTR | N-KTRTKFLKKTAhxβAla-COOH | 82 |
| KFF | N-KFFKFFKFFAhxβAla-COOH | 83 |
| KFFK | N-KFFKFFKFFKAhxβAla-COOH | 84 |
| (RFF)$_2$ | N-RFFRFFAhxβAla-COOH | 85 |
| (RFF)$_2$R | N-RFFRFFRAhxβAla-COOH | 86 |
| RAhx | N-RAhxAhxRAhxAhxRAhxAhxβAla-COOH | 87 |
| RFF-AcpP11 | N-RFFRFFRFFAhxβAla-CTTCGATAGTG-3' | 88 |

TABLE 4-continued

Peptide and Peptide-PMO Sequences

| Name | Sequence (Amino to Carboxy Terminus, 5' to 3') | SEQ ID NO |
|---|---|---|
| RTR-AcpP11 | N-RTRTRFLRRTAhxβAla-CTTCGATAGTG-3' | 89 |
| RFFR-AcpP11 | N-RFFRFFRFFRAhxβAla-CTTCGATAGTG-3' | 90 |
| (RFF)$_2$-AcpP11 | N-RFFRFFAhxβAla-CTTCGATAGTG | 91 |
| (RFF)$_2$R-AcpP11 | N-RFFRFFRAhxβAla-CTTCGATAGTG | 92 |
| RAhx-AcpP11 | N-RAhxAhxRAhxAhxRAhxAhxβAla-CTTCGATAGTG | 93 |

EXAMPLE 1

Acyl Carrier Protein as an Endogenous Bacterial Gene Target

The effect of PMO was tested on an endogenous bacterial gene that encodes acyl carrier protein, acpP, which is essential for viability (Zhang and Cronan 1996) and has been used previously to inhibit bacterial growth (Good, Awasthi et al. 2001; Geller, Deere et al. 2003). PMO from 6 to 20 bases in length and complementary to the region around the start codon in mRNA for acpP (Table 3, SEQ ID NOS:62-71, respectively) were added to growing cultures of AS19 and growth at 37° C. was monitored by optical density and viable cell counts. Growth curves were normal for all cultures except for that with the 11 base PMO, which caused significant inhibition (FIG. 3A). Slight and reproducible, but statistically insignificant inhibitions of OD occurred in cultures with the 10 and 14 base PMO. Viable cells were significantly reduced in 8 hour cultures that contained PMO of 10, 11 or 14 bases (FIG. 3B). No reduction in CFU was apparent in cultures treated with PMO of less than 10 or more than 14 bases in length. Cultures without PMO, or with nonsense base sequences (7c, 14c and 20c; SEQ ID NOS:76, 74 and 72, respectively) did not demonstrate growth inhibition.

PMO of various lengths (from 6 to 20 bases; SEQ ID NOS:62-71, respectively) and targeted to acpP were added to bacterial, cell-free protein synthesis reactions programmed to express an acpP-luc fusion reporter. The results (FIG. 4) show that PMO 11 to 20 bases in length inhibited reporter expression to about the same extent. PMO shorter than 11 bases in length, or nonsense sequence controls (16c and 20c; SEQ ID NOS:73 and 72, respectively) did not inhibit luciferase expression significantly.

EXAMPLE 2

In vivo Antisense Antibacterial Activity

Groups of 12 mice in each of three treatment groups were injected IP with E. coli strain AS19, which has a genetic defect that makes it abnormally permeable to high MW solutes. Immediately following infection, each mouse was injected IP with 300 μg of an 11-base PMO complementary to acpP (PMO 169; SEQ ID NO:66), an 11-base nonsense sequence control PMO (PMO 170; SEQ ID NO:75), or PBS. Peritoneal ravages were collected at 2, 7, 13, and 23 hours post-infection, and plated for bacteria. The results show that at all times analyzed, the acpP PMO-treated mice had significantly (P<0.05) lower CFU than the mice treated with either nonsense PMO or PBS (FIG. 5). The differences between the acpP PMO-treated group and the nonsense PMO control ranges from 39-fold at 2 hours to 600-fold at 23 hours.

The same PMOs were again tested, except with E. coli strain SM105, which has a normal outer membrane. AcpP PMO reduced CFU by 84% compared to nonsense PMO at 12 hours post-infection. There was no reduction of CFU at 2, 6, or 24 hours (FIG. 6). Mice were injected with a second dose at 24 hours post-infection. By 4 hours post-infection the CFU of acpP PMO-treated mice were 70% lower than the CFU of nonsense PMO-treated mice (FIG. 6).

The above results with acpP and nonsense PMOs suggest that inhibition was sequence specific. To demonstrate directly a sequence-specific effect, mice were infected with an E. coli AS19 that expresses firefly luciferase, then treated at 0 and 13 hours post-infection with a PMO (luc; SEQ ID NO:77) complementary to the region around the start codon of the luciferase transcript, or a nonsense PMO (luc nonsense; SEQ ID NO:78). Peritoneal lavages were collected at 13 and 22 hours post-infection and analyzed for CFU, luciferase activity, and luciferase and OmpA protein by western immunoblot analysis. As expected, the results show no inhibition of growth with the luc PMO treatment compared to nonsense PMO treatment (Table 5). Luciferase activity in samples from luc PMO-treated mice was inhibited 53% and 46% at 13 and 22 hours, respectively, compared to samples from nonsense PMO-treated mice (Table 5).

Western blot analysis agreed closely with the results of luciferase activity. In samples from luc PMO-treated mice, there was a 68% and 47% reduction in the amount of luciferase protein at 13 and 22 hours, respectively, compared to samples from nonsense PMO-treated mice (Table 5).

TABLE 5

| | | | Gene Specific Inhibition | | | | | |
|---|---|---|---|---|---|---|---|---|
| | | | Luciferase Activity | | | Western Blot | | |
| PMO Treatment | Time after treatment (h) | CFU/ml (×10$^6$) | RLU/CFU Mean (SEM) n = 8 | P | % Inhibition | Luc/OmpA Mean (SEM) n = 7-8 | P | % Inhibition |
| Luc | 13 | 6.3 | 2.90 (0.629) | .0035 | 53 | 0.122 (.0312) | .0002 | 68 |
| Nonsense | 13 | 4.3 | 6.19 (0.773) | | 0 | 0.382 (.0296) | | 0 |

TABLE 5-continued

| | | | Gene Specific Inhibition | | | | | |
|---|---|---|---|---|---|---|---|---|
| | | | Luciferase Activity | | | Western Blot | | |
| PMO Treatment | Time after treatment (h) | CFU/ml (×10$^6$) | RLU/CFU Mean (SEM) n = 8 | P | % Inhibition | Luc/OmpA Mean (SEM) n = 7-8 | P | % Inhibition |
| Luc | 22 | 0.96 | 3.20 (0.582) | .0093 | 46 | 0.147 (.0363) | .0145 | 57 |
| Nonsense | 22 | 0.39 | 8.12* (1.94) | | 0 | 0.339 (.0668) | | 0 |

EXAMPLE 3

Enhanced Anti-bacterial Properties of Peptide-conjugated PMO

PMO conjugated at the 5' terminus with a series of three different peptides were evaluated for their antibacterial properties. The 11 mer PMO that targets the *E. coli* acpP gene (SEQ ID NO:66) was used as the antisense oligomer moiety and conjugated to either the RFF, RTR or RAhx peptides (SEQ ID NOS:79-80 and SEQ ID NO:87, respectively) to produce peptide-conjugated PMOs (P-PMOs) RFF-AcpP11, RTR-AcpP11 and RAhx-AcpP11 (SEQ ID NOS:88-89 and SEQ ID NO:93, respectively).

Figure 11:
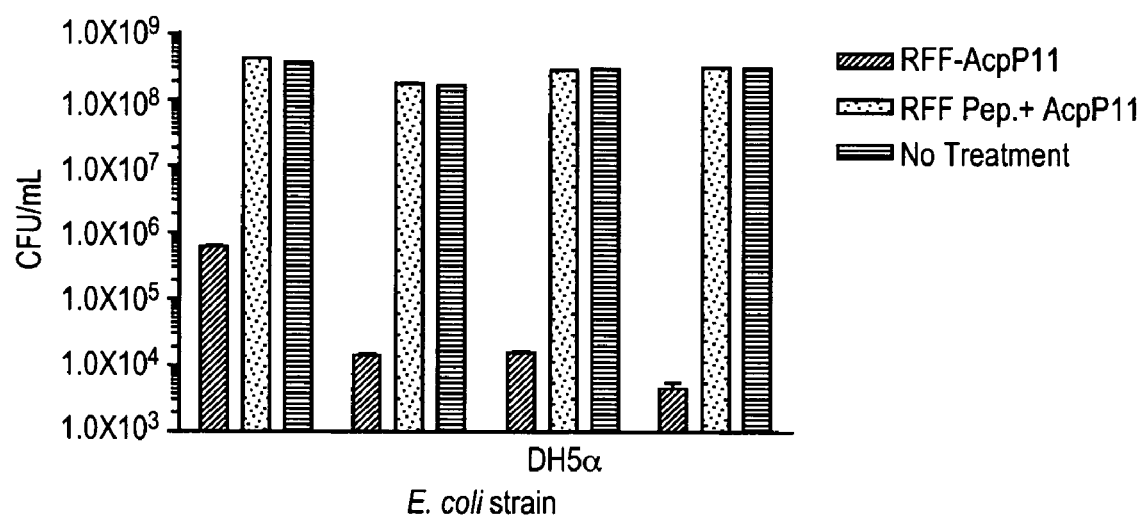
FIG. 11 shows the colony-forming units per milliliter (CFU/ml) of four strains of *E. coli* after eight hours incubation in the presence of the RFF-AcpP11 P-PMO compared to no treatment and treatment with a mixture of the AcpP11 PMO and the RFF peptide.

Four laboratory strains of *E. coli* (W3110, MIC2067, DH5α, SM105) were treated with 20 μM RFF-AcpP11 PPMO (SEQ ID NO:88), 20 μM free RFF peptide (SEQ ID NO:79) with unconjugated AcpP11 PMO (SEQ ID NO:66), or received no treatment (control) in LB broth, then were incubated at 37° C. for 24 hours. Every hour for 8 hours then at 24 hours the OD600 values (turbidity measurement) of the cultures were measured using a spectrophotometer. After 8 hours, aliquots of the cultures were diluted then plated onto LB agar plates and incubated for 24 hours at 37° C. After incubation, the colonies were counted by hand and the colony formation units/mL (CFU/mL) for each treatment were calculated. FIGS. 7 to 10 show the 24 hour growth curves for strains W3110, MIC2067, DH5α and SM105, respectively, in the presence of the RFF-AcpP11 P-PMO. FIG. 11 shows the CFU/ml after 8 hours treatment for the four strains of *E. coli*.

Using identical conditions as described above, *E. coli* W3110 was treated with three different P-PMOs (RAhx-AcpP11, RTR-AcpP11 and RFF-AcpP11) or received no treatment. FIG. 12 shows the CFU/ml after 8 hours of treatment with the three different P-PMOs compared to no treatment.

*E. coli* W3110 was treated with a short dilution series of RFF peptide at 5 μM, 20 μM, 50 μM and 100 μM, 20 μM RFF free peptide mixed with AcpP11 PMO, 20 μM RFF-AcpP11 P-PMO, 10 μM ampicillin or no treatment. FIG. 13 shows the CFU/ml after 8 hours for each treatment. This data strongly supports the conclusion that only the P-PMO and ampicillin showed antibacterial activity and that the delivery peptide must be conjugated to the PMO for this effect. Furthermore, the RFF-AcpP11 P-PMO demonstrates an approximately 10 fold improved antibacterial activity at 10 μM compared to ampicillin at the same concentration.

A series of dose-response experiments were performed where *E coli* W3110 was exposed to RFF-AcpP11, RTR-AcpP11, and ampicillin in pure culture. *E coli* W3110 was treated with a dilution series of RFF-AcpP11, RTR-AcpP11 or ampicillin (80 μM, 40 μM, 20 μM, 10 μM, 5 μM, 2.5 μM) or received no treatment. Determination of 50% inhibitory concentration values (IC$_{50}$) for RFF-AcpP11, RTR-AcpP11, and ampicillin were made using standard methods. FIG. 14 shows the dose response curves for each of the two PPMOs compared to ampicillin and the associated IC$_{50}$ values of 3.7, 12.1 and 7.7 mM for RFF-AcpP11, RTR-AcpP11 and ampicillin, respectively.

Figure 15:
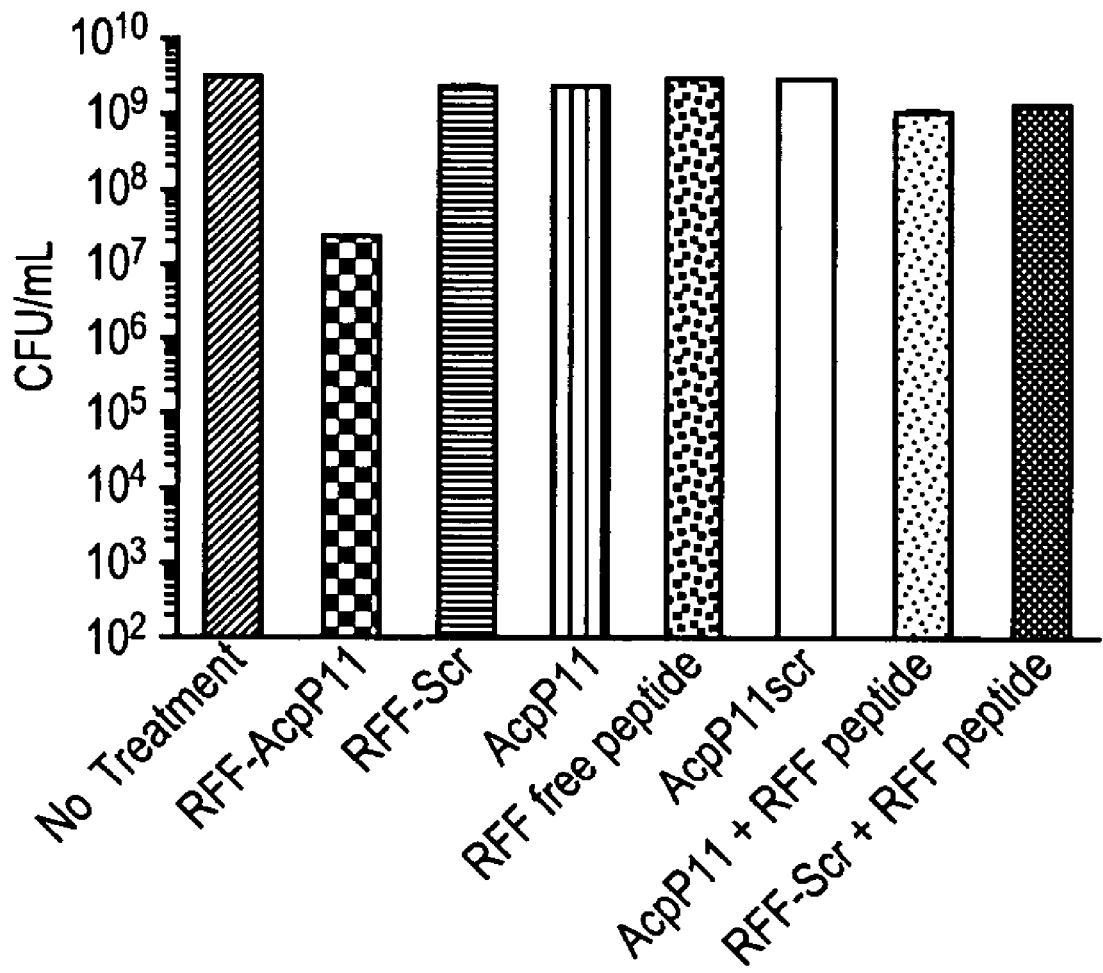
FIGS. 15 and 16 show the effect of RFF-AcpP11 P-PMO on *S. typhimurium* and an enterpathogenic strain of *E. coli* (O127:H6) as measured by CFU/ml after eight hours of treatment compared to no treatment, AcpP11 alone, RFF peptide alone, scrambled controls, and a mixture of AcpP11 and RFF peptide.
Figure 16:
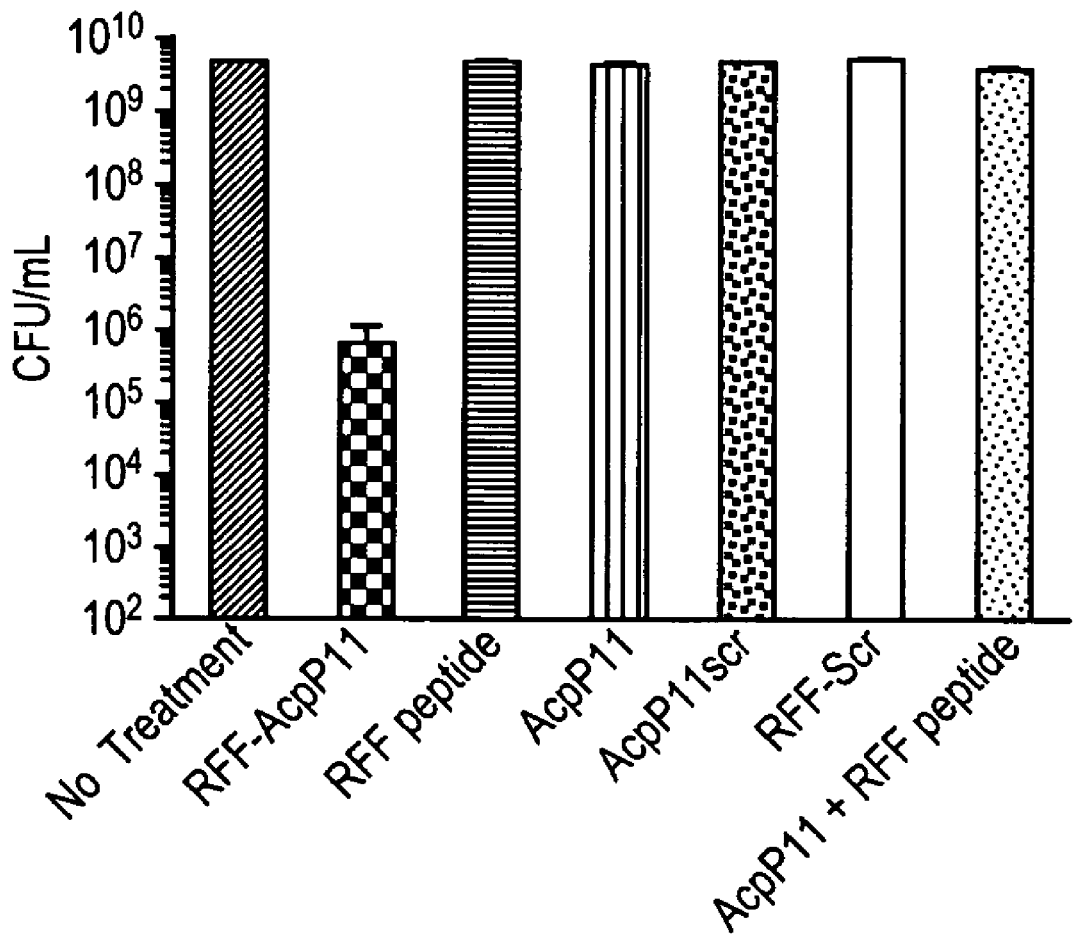

The sensitivity of *Salmonella typhimurium* 1535 and a clinically isolated enterpathogenic strain of *E. coli* (EPEC strain O127:H6) to RFF-AcpP11 P-PMO in culture was determined. The target sequences for AcpP11 (SEQ ID NOS:2 and 8) in *S. typhimurium* and *E. coli* are identical. Both strains were treated with 20 μM of RFF-AcpP11 P-PMO, RFF free peptide mixed with unconjugated AcpP11 PMO, AcpP11 scr PMO, RFF-Scr P-PMO, RFF free peptide mixed with unconjugate AcpP11 PMO or no treatment. FIGS. 15 and 16 show the CFU/mL after 8 hours treatment for *S. typhimurium* and EPEC strain O127:H6. This data clearly demonstrate the utility of the RFF-AcpP11 compound as an antibacterial agent against clinically relevant bacterial isolates.

EXAMPLE 4

Antibacterial Activity of Peptide-conjugated PMO Targeting *Burkholderia* and *Pseudomonas* Species

Figure 17:
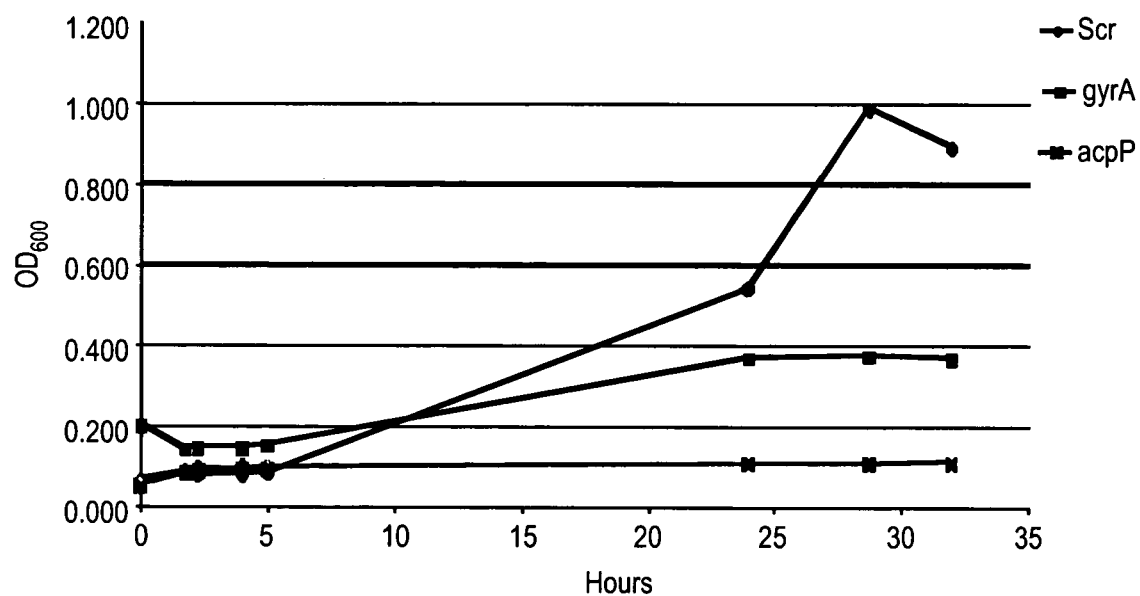
FIGS. 17 and 18 show the effect of RFFR-conjugated PMOs on the growth of *Burkholderia cenocepacia* and *Pseudomonas aeruginosa*, respectively.

*Burkholderia cenocepacia* growth in the presence of peptide-conjugated PMO was determined using the compounds of the invention. A stationary phase culture of *B. cenocepacia* was diluted to 5×10$^5$ cfu/ml in Mueller-Hinton broth. The peptide-conjugated PMO that target the acpP and gyrA genes were added to identical cultures to a final concentration of 200 μmol/L. The cultures were grown aerobically at 37° C. and optical density was monitored. After 36 hours, each culture was diluted and plated to determine viable cell count as colony forming units per ml (CFU/ml). All peptide-conjugated PMOs had the same peptide attached to the 5' end, which was (RFF)$_3$RAhxβAla(SEQ ID NO:81). All PMOs were 11 bases in length and targeted to regions around the start codon of acyl carrier protein (acpP) or the DNA gyrase subunit A (gyrA) as described above. Scr is a negative control, scrambled base sequence peptide-conjugated PMO that has no complementary target in *B. cenocepacia*. FIG. 17 shows the inhibition of *Burkholderia cenocepacia* growth, as measured by optical density, by the gyrA and acpP peptide-conjugated PMO compared to the Scr control. The viable cell count after 36 hours treatment was less than 1×10$^4$ CFU/ml for the peptide-conjugated PMOs targeting the acpP and gyrA genes whereas for the Scr control peptide-conjugated PMO the viable cell count was 8.5×10$^7$ CFU/ml. Similar results were obtained using these PMO against *B. multivorans* and *B. gen.II*.

Figure 18:
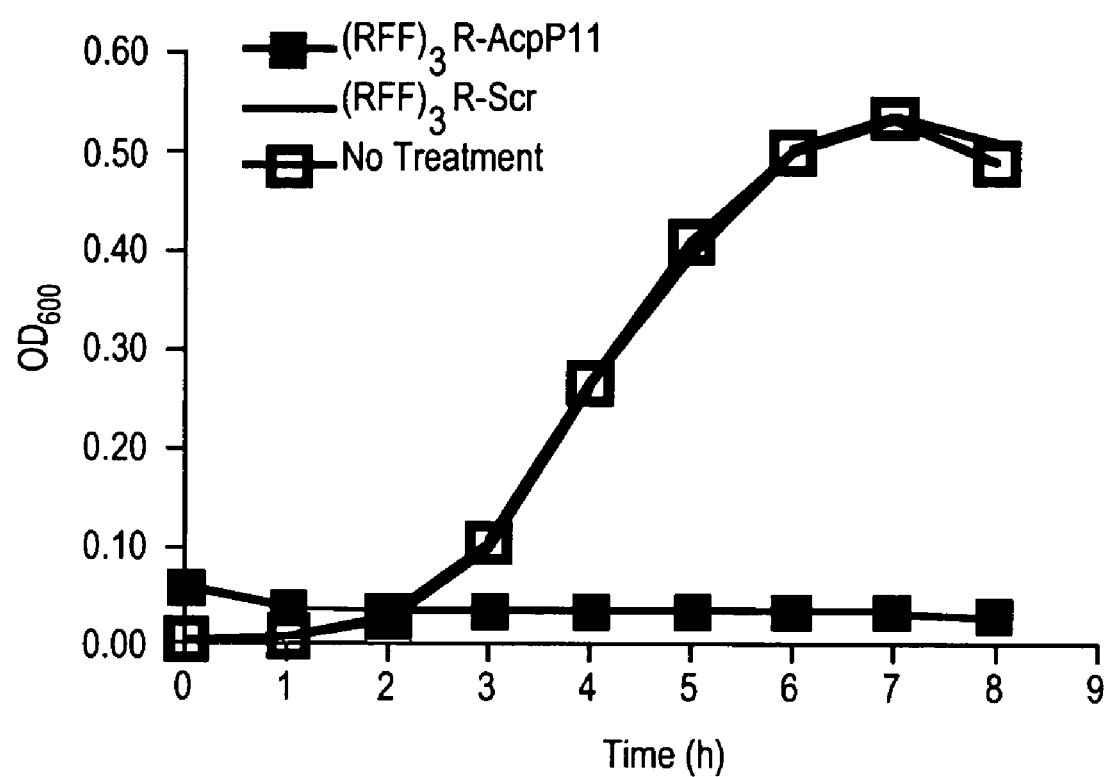

Similar experiments targeting *Pseudomonas aeruginosa* using RFFR (SEQ ID NO:81) conjugated to a PMO that targets the *P. aeruginosa* acpp gene. The RFFR-AcpP PMO targeted to acpp was added to a growing culture of *P. aeruginosa* in Mueller-Hinton broth at a 20 micromolar concentration. Aerobic growth at 37° C. was measured by optical density at 600 nm. The results shown in FIG. 18 show complete inhibition of growth and the scrambled base sequence control had no effect on growth.

SEQUENCE LISTING:

| Name | Sequence (5' to 3') or (amino to carboxyl) | SEQ ID NO |
|---|---|---|
| *E. coli* ftsZ | GAGAGAAACTATGTTTGAACCAATGGAACTT | 1 |
| *E. coli* acpP | ATTTAAGAGTATGAGCACTATCGAAGAACGC | 2 |
| *E. coli* gyrA | TAGCGGTTAGATGAGCGACCTTGCGAGAGAA | 3 |
| *E. coli* O157:H7 ftsZ | GAGAGAAACTATGTTTGAACCAATGGAACTT | 4 |
| *E. coli* O157:H7 acpP | ATTTAAGAGTATGAGCACTATCGAAGAACGC | 5 |
| *E. coli* O157:H7 gyrA | TAGCGGTTAGATGAGCGACCTTGCGAGAGAA | 6 |
| *S. typhimurium* ftsZ | GAGAGAGATTATGTTTGAACCTATGGAACTA | 7 |
| *S. typhimurium* acpP | ATTTAAGAGTATGAGCACTATCGAAGAACGC | 8 |
| *S. typhimurium* gyrA | TAGCGGTTAGATGAGCGACCTTGCGAGAGAA | 9 |
| *P. aeruginosa* ftsZ | GAGAGGGGAAATGTTTGAACTGGTCGATAAC | 10 |
| *P. aeruginosa* acpP | AAAACAAGGTATGAGCACCATCGAAGAACGC | 11 |
| *P. aeruginosa* gyrA | CAGGCTTCTCATGGGCGAACTGGCCAAAGAA | 12 |
| *V. cholera* ftsZ | GAGATAACACATGTTTGAACCGATGATGGAA | 13 |
| *V. cholera* acpP | ACTATATTGGATGGTTTATATGTCTATCTCT | 14 |
| *V. cholera* gyrA | TAATGGCTCTATGAGCGATCTAGCTAAAGAG | 15 |
| *N. ghonorrhoea* ftsZ | GAGTTTTTGAATGGAATTTGTTTACGACGT | 16 |
| *N. ghonorrhoea* acpP | AACGACTGATATGTCAAACATCGAACAACA | 17 |
| *N. ghonorrhoea* gyrA | CATTGAAACCATGACCGACGCAACCATCCG | 18 |
| *S. aureus* ftsZ | GGAAATTTAAATGTTAGAATTTGAACAAGGA | 19 |
| *S. aureus* gyrA | GGAACTCTTGATGGCTGAATTACCTCAATCA | 20 |
| *S. aureus* fmhB | ATCATAAATCATGGAAAAGATGCATATCAC | 21 |
| *M. tuberculosis* ftsZ | CTCTAAGCCTATGGTTGAGGTTGAGAGTTTG | 22 |
| *M. tuberculosis* acpP | CCCGGGCGCGATGTGGCGATATCCACTAAGT | 23 |
| *M. tuberculosis* gyrA | CGAGGAATAGATGACAGACACGACGTTGCCG | 24 |
| *M. tuberculosis* pimA | GGAAAGCCTGATGCGGATCGGCATGATTTG | 25 |
| *M. tuberculosis* cysS2 | CTGGCACGTCGTGACCGATCGGGCTCGCTT | 26 |
| *H. pylori* ftsZ | GAATGTGGCTATGGTTCATCAATCAGAGATG | 27 |
| *H. pylori* acpP | AGTTTTAATTATGGCTTTATTTGAAGATATT | 28 |
| *H. pylori* gyrA | AGGGAGACACATGCAAGATAATTCAGTCAAT | 29 |
| *S. pneumoniae* ftsZ | AAAATAAATTATGACATTTTCATTTGATACA | 30 |
| *S. pneumoniae* acpP | GAGTCCTATCATGGCAGTATTTGAAAAAGTA | 31 |
| *S. pneumoniae* gyrA | GCATTTATTAATGCAGGATAAAAATTTAGTG | 32 |
| *T. palladium* ftsZ | TGGGAGGGGAATGATGAATATAGAGCTTGCA | 33 |
| *T. palladium* acpP | TGCCCCGTGGATGAGTTGTTCTTAAGAATGA | 34 |
| *T. palladium* gyrA | TGCCCGCCCTATGGAAGAAATTAGCACCCCA | 35 |
| *C. trachomatis* acpP | GGATCATAGGATGAGTTTAGAAGATGATGTA | 36 |
| *C. trachomatis* gyrA | AAACGAACTTATGAGCGACCTCTCGGACCTA | 37 |
| *B. henselae* ftsZ | AGGCAAATTAATTGGTAAAAAATTAGAGAG | 38 |
| *B. henselae* acpP | GGATTTCAACATGAGTGATACAGTAGAGCG | 39 |
| *B. henselae* gyrA | GTCTAAAGCTGTGACAGATCTAAACCCGCA | 40 |
| *H. influenza* ftsZ | GAGAACATCAATGCTATACCCAGAGTACCCT | 41 |
| *H. influenza* acpP | GGAAAAACAAATGAGTATTGAAGAACGCGTG | 42 |
| *H. influenza* gyrA | AGGAATACCAATGACGGATTCAATCCAATCA | 43 |
| *L. monocytogenes* ftsZ | AGGCAATAATATGTTAGAATTTGACACTAG | 44 |
| *L. monocytogenes* | CGAACGCATAAAACTTTATGTGACCGGATA | 45 |
| *L. monocytogenes* | TTCTCTAACAATGGCAGAAACACCAAATCA | 46 |
| *Y. pestis* ftsZ | GAGAGAAACTATGTTTGAACCTATGGAACT | 47 |
| *Y. pestis* acpP | ATTTAAGAGTATGAGCACTATCGAAGAACG | 48 |
| *Y. pestis* gyrA | TAGCGGCTCAATGAGCGACCTTGCCAGAGA | 49 |
| *B. anthracis* ftsZ | GGATTTCGACATGTTAGAGTTTGATACTAC | 50 |
| *B. anthracis* acpP | GGTGAATGGAATGGCAGATGTTTTAGAGCG | 51 |
| *B. anthracis* gyrA | GTGCTCGTTGATGTCAGACAATCAACAACA | 52 |
| *B. mallei* ftsZ | GGAGGCAACAATGGAATTCGAAATGCTGGA | 53 |
| *B. mallei* acpP | CGGAGGGGTAATGGACAACATCGAACAACG | 54 |
| *B. mallei* gyrA | ATACGGATACATGGATCAATTCGCCAAAGA | 55 |
| *B. pseudomallei* ftsZ | GGAGGCAACAATGGAATTCGAAATGCTGGA | 56 |
| *B. pseudomallei* acpP | CGGAGGGGTAATGGACAACATCGAACAACG | 57 |
| *B. pseudomallei* gyrA | ATACGGATACATGGATCAATTCGCCAAAGA | 58 |
| *F. tularensis* ftsZ | GGAGTAAAATATGTTTGATTTTAACGATTC | 59 |
| *F. tularensis* acpP | AGGAAAAAATATGAGTACACATAACGAAGA | 60 |
| *F. tularensis* gyrA | GCGATAACTAATGTCTATAATTACTAAAGA | 61 |
| 62-1 | TTCTTCGATAGTGCTCATAC | 62 |
| 62-2 | TCTTCGATAGTGCTCATA | 63 |
| 62-3 | CTTCGATAGTGCTCAT | 64 |
| 62-4 | TCGATAGTGCTCAT | 65 |
| 169 (acpP, +5 to +15) | CTTCGATAGTG | 66 |
| 379 | TTCGATAGTG | 67 |
| 380 | TTCGATAGT | 68 |
| 381 | TCGATAGT | 69 |

SEQUENCE LISTING:

| Name | Sequence (5' to 3') or (amino to carboxyl) | SEQ ID NO |
|---|---|---|
| 382 | TCGATAG | 70 |
| 383 | CGATAG | 71 |
| 62-5 | TTGTCCTGAATATCACTTCG | 72 |
| 62-7 | GTCCTGAATATCACTT | 73 |
| 62-8 | TCGTGAGTATCACT | 74 |
| 170 | TCTCAGATGGT | 75 |
| 384 | AATCGGA | 76 |
| Luc | ACGTTGAGGC | 77 |
| Luc-nonsense | TCCACTTGCC | 78 |
| RFF | N-RFFRFFRFFAhxβAla-COOH | 79 |
| RTR | N-RTRTRFLRRTAhxβAla-COOH | 80 |
| RFFR | N-RFFRFFRFFRAhxβAla-COOH | 81 |
| KTR | N-KTRTKFLKKTAhxβAla-COOH | 82 |
| KFF | N-KFFKFFKFFAhxβAla-COOH | 83 |
| KFFK | N-KFFKFFKFFKAhxβAla-COOH | 84 |
| (RFF)$_2$ | N-RFFRFFAhxβAla-COOH | 85 |
| (RFF)$_2$R | N-RFFRFFRAhxβAla-COOH | 86 |
| RAhx | N-RAhxAhxRAhxAhxRAhxAhxβAla-COOH | 87 |
| RFF-AcpP11 | N-RFFRFFRFFAhxβAla-CTTCGATAGTG | 88 |
| RTR-AcpP11 | N-RTRTRFLRRTAhxβAla-CTTCGATAGTG | 89 |
| RFFR-AcpP11 | N-RFFRFFRFFRAhxβAla-CTTCGATAGTG | 90 |
| (RFF)$_2$-AcpP11 | N-RFFRFFAhxβAla-CTTCGATAGTG | 91 |
| (RFF)$_2$R-AcpP11 | N-RFFRFFRAhxβAla-CTTCGATAGTG | 92 |
| RAhx-AcpP11 | N-RAhxAhxRAhxAhxRAhxAhxβAla-CTTCGATAGTG | 93 |
| acpP (−4 to +7) | TGCTCATACTC | 94 |
| acpP (+1 to +11) | ATAGTGCTCAT | 95 |
| acpP (+11 to +21) | GCGTTCTTCCG | 96 |

---

The invention claimed is:

1. An antibacterial antisense conjugate for use in treating a bacterial infection in a mammalian host, comprising (a) a substantially uncharged antisense oligonucleotide composed of morpholino subunits and phosphorus-containing intersubunit linkages joining a morpholino nitrogen of one subunit to a 5' exocyclic carbon of an adjacent subunit, having between 10-20 bases and a targeting sequence of at least 10 contiguous bases complementary to a target region of the infecting bacteria's mRNA for acyl carrier protein (acpP), where the target region contains the translational start codon of the bacterial mRNA, or a sequence that is within 20 bases, in a downstream direction, of the translational start codon, and where the oligonucleotide binds to the mRNA to form a heteroduplex having a $T_m$ of at least 50° C., thereby to inhibit replication of the bacteria, and (b) conjugated to the oligonucleotide, a carrier peptide that is (i) represented by the sequence $(RFF)_nR$- or the sequence $(RXX)_n$-, where X is an uncharged amino acid selected from the group consisting of alanine, β-alanine, valine, leucine, isoleucine, serine, threonine, phenylalanine, and tryptophan, and n=2 or 3, and (ii) coupled to the oligonucleotide at the peptide's C terminus.

2. The conjugate of claim 1, wherein the carrier peptide has the form $(RFF)_n$.

3. The conjugate of claim 1, wherein the carrier peptide has the form $(RFF)_nR$-.

4. The conjugate of claim 1, wherein the carrier peptide is linked at its C-terminus to the 5' end of the oligonucleotide through a one- or two-amino acid linker.

5. The conjugate of claim 4, wherein the linker is AhxβAla, where Ahx is 6-aminohexanoic acid and βAla is β-alanine.

6. The conjugate of claim 1, wherein the carrier peptide has the ability, when conjugated to the 5' end of a phosphorodiamidate-linked morpholino oligomer (PMO) having SEQ ID NO: 66, to enhance the anti-bacterial activity of the PMO by a factor of at least 10, as measured by the reduction in bacterial colony-forming units/ml (CFU/ml) when the peptide-conjugated PMO compound is added at a concentration of 20 µM in a culture to *E. coli*, strain W3110 at $5 \times 10^7$ CFU/ml in Luria broth for a period of 8 hours at 37° C. with aeration, relative to the same activity of the PMO oligonucleotide alone.

7. The conjugate of claim 1, wherein the carrier peptide has the ability to enhance the anti-bacterial activity of said PMO by a factor of at least $10^2$, under the claimed conditions.

8. The conjugate of claim 1, wherein the morpholino subunits in the oligonucleotide are joined by phosphorodiamidate linkages, in accordance with the structure:

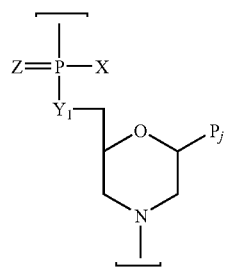

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

* * * * *

UNITED STATES PATENT AND TRADEMARK OFFICE
CERTIFICATE OF CORRECTION

| | | |
|---|---|---|
| PATENT NO. | : 7,790,694 B2 | Page 1 of 1 |
| APPLICATION NO. | : 11/487009 | |
| DATED | : September 7, 2010 | |
| INVENTOR(S) | : Bruce L. Geller et al. | |

It is certified that error appears in the above-identified patent and that said Letters Patent is hereby corrected as shown below:

Column 68
Claim 4, Line 59, "The conjugate of claim 1, whereinthe carrier peptide is" should read as --The conjugate of claim 1, wherein the carrier peptide is--.

Signed and Sealed this
First Day of March, 2011

David J. Kappos
*Director of the United States Patent and Trademark Office*